(12) United States Patent
Kleemann et al.

(10) Patent No.: US 6,486,189 B2
(45) Date of Patent: Nov. 26, 2002

(54) FIVE-MEMBERED HETEROCYCLES HAVING BIPHENYLSULFONYL SUBSTITUTION, PROCESS FOR THEIR PREPARATION, THEIR USE AS A MEDICAMENT OR DIAGNOSTIC, AND MEDICAMENT COMPRISING THEM

(75) Inventors: Heinz-Werner Kleemann, Bischofsheim (DE); Hans Jochen Lang, Hofheim (DE); Jan-Robert Schwark, Frankfurt (DE); Andreas Weichert, Egelsbach (DE); Sabine Faber, Idstein (DE); Hans-Willi Jansen, Niedernhausen (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/984,469

(22) Filed: Oct. 30, 2001

(65) Prior Publication Data

US 2002/0045761 A1 Apr. 18, 2002

Related U.S. Application Data

(63) Continuation of application No. 09/010,181, filed on Jan. 21, 1998, now Pat. No. 6,335,451.

(30) Foreign Application Priority Data

Jan. 22, 1997 (DE) ......................... 197 02 045
Jul. 22, 1997 (DE) ......................... 197 31 328
Sep. 22, 1997 (DE) ......................... 197 41 636

(51) Int. Cl.$^7$ ........................................ A61K 31/4164
(52) U.S. Cl. ........................ 514/386; 514/398; 514/399; 514/400
(58) Field of Search ............................... 514/386, 398, 514/399, 400

(56) References Cited

U.S. PATENT DOCUMENTS

| | | | |
|---|---|---|---|
| 5,281,614 A | 1/1994 | Ashton et al. | |
| 5,391,732 A | 2/1995 | Bhatnagar et al. | |
| 5,412,101 A | 5/1995 | Caille et al. | |
| 5,482,957 A | 1/1996 | Wagner et al. | |
| 5,527,919 A | 6/1996 | Bhatnagar et al. | |
| 5,599,830 A | 2/1997 | Caille et al. | |
| 5,604,251 A | 2/1997 | Heitsch et al. | |
| 5,684,028 A | 11/1997 | Caille et al. | |
| 6,335,451 B1 | 1/2002 | Kleemann et al. | 548/320.5 |

FOREIGN PATENT DOCUMENTS

| | | |
|---|---|---|
| EP | 0465368 | 1/1992 |
| EP | 0479479 | 4/1992 |
| EP | 0503162 | 9/1992 |
| EP | 0648763 | 4/1995 |
| WO | WO 92/20662 | 11/1992 |
| WO | WO 95/23791 | 9/1995 |
| WO | WO 95/23792 | 9/1995 |
| WO | WO 97/13513 | 4/1997 |
| WO | WO 97/21436 | 6/1997 |

OTHER PUBLICATIONS

Deprez et al., "Sulfonylureas and Sulfonylcarbamates as New Non–Tetrazole Angiotensin II Receptor Antagonists, Discovery of a Highly Potent Orally Active (Imidazolylbiphenylyl)sulfonylurea (HR 720)," J. Med. Chem., 38:2357–2377 (1995).

Ashton et al., "Triazolinone Biphenylsulfonamide Derivatives as Orally Active Angiotensin II Antagonists with Potent AT, Receptor Affinity and Enchanched AT$_2$ Affinity [1,2]," J. Med. Chem., 37:2808–2824 (1994).

Matsumura et al. "Studies of Nitriles. XI. Preparation and Chemistry of Schiff Bases of ADAN, 2–Amino–3,3–dichloroacrylonitrile. A highly Effective Conversion into 2–Substituted–4(5)–chloroimidazole–5(4)–carbaldehydes," Chem. Pharm. Bull. 24(5):960–969 (1976).

Almansa et al., "Synthesis and Structure—Activity Relationship of a New Series of Potent AT, Selective Angiotensin II Receptor Antagonists: 5–(Biphenyl–4–ylmethyl)pyrozoles," J. Med. Chem. 40:547–558 (1997).

Derwent Abstract of EP 0648763, 1994.

Faber et al., "A Novel Screening Assay of the Na+–Dependent CI–/HCO$_3$–Exchanger (NCBE) and its Inhibitors", Cell Physiol. Biochem., 6:39–49 (1996).

(List continued on next page.)

Primary Examiner—Laura L. Stockton
(74) Attorney, Agent, or Firm—Finnegan, Henderson, Farabow, Garrett & Dunner, LLP

(57) ABSTRACT

Five-membered heterocycles having biphenylsulfonyl substitution, process for their preparation, their use as a medicament or diagnostic, and medicament comprising them. Compounds of the formula I

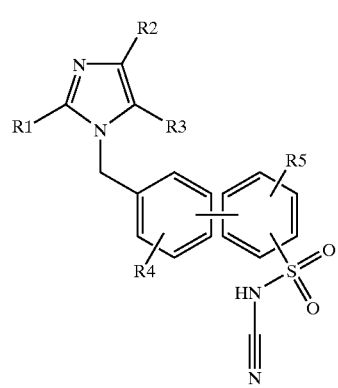

in which the symbols have the meanings indicated in the claims, have outstanding antiarrhythmic properties and exhibit a cardioprotective component. They can preventively inhibit or greatly decrease the pathophysiological processes in the formation of ischemically induced damage, in particular in the elicitation of ischemically induced cardiac arrhythmias. Moreover, they have a potent inhibitory action on the proliferation of cells.

12 Claims, No Drawings

OTHER PUBLICATIONS

Fernandez et al., "Angiotensin AT(2) Receptor Stimulation Increases Survival in Gerbils with Abrupt Unilateral Carotid Ligation," J. Cardiovasc. Pharmacol., vol. 124, No. 6, 1994, pp. 937–940.

Liu et al., "Paracrine Systems in the Cardioprotective Effect of Angiotensin–Converting Enzyme Inhibitors on Myocardial Ischemia/Reperfusion Injury in Rats," Hypertension, vol. 27, No. 1, 1996, pp. 7–13.

Thomas et al., "Losartan Exerts Antiarrhythmic Activity Independent of Angiotensin II Receptor Blockade in Simulated Ventricular Ischemia and Reperfusion," J. Pharmacol. Exp. Ther., vol. 278, No. 3, 1996, pp. 1090–1097.

Hartman et al., "Reduction of Myocardial Infarct Size by Ramiprilat is Independent of Angiotensin II Synthesis Inhibition," Eur. J. Pharmacol., vol. 234, No. 2–3, 1993, pp. 229–236.

Koke et al., "The Cardiac Renin–Angiotensin System and Myocardial Stunning in the Dog Heart," Biomed. Lett., vol. 48, No. 190, 1993, pp. 97–113.

Ford et al., "Opposite Effects of Angiotensin AT(1) and AT(2) Receptor Antagonists on Recovery of Mechanical Function After Ischemia–Reperfusion in Isolated Working Rat Hearts," Circulation, vol. 94, No. 12, 1996, pp. 3087–3089.

Heller et al., "Losartan Protects the Rat Kidney from Ischemic Injury," Kidney Int., vol. 49, No. Suppl. 55, 1996, pp. S113–S114.

Werrmann et al., "Use of Losartan to Examine the role of the Cardiac Renin–Angiotensin System in Myocardial Dysfunction During Ischemia and Reperfusion," J. Cardiovasc. Pharmacol., vol. 27, No. 2, 1996, pp. 177–182.

Patent Abstracts of Japan, vol. 018, No. 236, May 6, 1994 & JP 06 025229 A (Japan Tobacco Inc.), Feb. 1, 1994.

Patent Abstracts of Japan, vol. 012, No. 353, Sep. 21, 1988, & JP 63 107963 A (Toyama Chem. Co., Ltd.), May 12 1988.

Copy of co–pending patent application No. 09/010,181, filed on Jan. 21, 1998.

FIVE-MEMBERED HETEROCYCLES HAVING BIPHENYLSULFONYL SUBSTITUTION, PROCESS FOR THEIR PREPARATION, THEIR USE AS A MEDICAMENT OR DIAGNOSTIC, AND MEDICAMENT COMPRISING THEM

This is a continuation division of application Ser. No. 09/010,181, filed Jan. 21, 1998 now U.S. Pat. No. 6,335,451, which is incorporated herein by reference.

The invention relates to compounds of the formula I

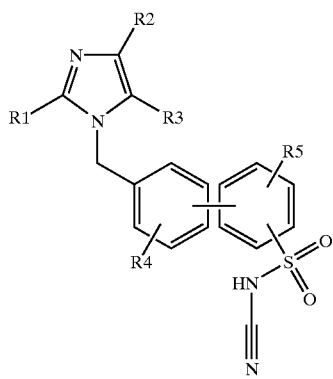

in which the symbols have the following meaning:

R1 is hydrogen, alkyl having 1, 2, 3, 4, 5, 6, 7 or 8 carbon atoms or —$C_aH_{2a}$—, phenyl,
said —$C_aH_{2a}$-phenyl being unsubstituted or substituted by 1–3 substituents selected from F, Cl, Br, 1, $CF_3$, methyl, methoxy, hydroxyl and NR(8)R(9);
R(8) and R(9) independently of one another are H or ($C_1$–$C_4$)alkyl;
a is zero, 1 or 2;

or

R1 is —$C_bH_{2b}$-($C_1$–$C_9$)heteroaryl, which is unsubstituted or substituted by 1–3 substituents selected from F, Cl, Br, I, $CF_3$, $CH_3$, methoxy, hydroxyl and NR(10)R(11);
R(10) and R(11) independently of one another are H or ($C_1$–$C_4$)alkyl;
b is zero, 1 or 2;

or

R1 is —$C_dH_{2d}$—($C_3$–$C_7$)cycloalkyl;
d is zero, 1 or 2;

R2 and R3
independently of one another are hydrogen, F, Cl, Br, I, $CF_3$, —C≡N, —$NO_2$, $CH_2OR17$, CO-R6 or O-R7;
R17 is hydrogen or alkyl having 1, 2, 3, 4, 5, 6, 7 or 8 carbon atoms
R6 is hydrogen, alkyl having 1, 2, 3, 4, 5, 6, 7 or 8 carbon atoms, OR30 or phenyl,
said phenyl being unsubstituted or substituted by 1–3 substituents selected from the group consistng of F, Cl, Br, I, $CF_3$, methyl, methoxy, hydroxyl and NR(31)R(32);
R(31) and R(32) independently of one another are H or ($C_1$–$C_4$)-alkyl;
R30 is hydrogen or alkyl having 1, 2, 3, 4, 5, 6, 7 or 8 carbon atoms;
R7 is hydrogen, alkyl having 1, 2, 3, 4, 5, 6, 7 or 8 carbon atoms, or phenyl,
said phenyl being unsubstituted or substituted by 1–3 substituents selected from F, Cl, Br, I, $CF_3$, methyl, methoxy, hydroxyl and NR(12)R(13);
R(12) and R(13) independently of one another are H or ($C_1$–$C_4$)-alkyl;

or

R7 is ($C_1$–$C_9$)heteroaryl,
which is unsubstituted or substituted by 1–3 substituents selected from F, Cl, Br, I, $CF_3$, $CH_3$, methoxy, hydroxyl and NR(14)R(15);
R(14) and R(15) independently of one another are H or ($C_1$–$C_4$)-alkyl;

or

R2 and R3
independently of one another are alkyl having 1, 2, 3, 4, 5, 6, 7 or 8 carbon atoms, cycloalkyl having 3, 4, 5, 6 or 7 carbon atoms or —$C_gH_{2g}$-phenyl,
said —$C_gH_{2g}$-phenyl being unsubstituted or substituted by 1–3 substituents selected from F, Cl, Br, I, $CF_3$, methyl, methoxy, hydroxyl and NR(18)R(19);
R(18) and R(19) independently of one another are H or ($C_1$–$C_4$)alkyl;
g is zero, 1 or 2;

or

R2 and R3
independently of one another are —$ClH_{2l}$—($C_1$–$C_9$)heteroaryl,
which is unsubstituted or substituted by 1–3 substituents selected from F, Cl, Br, I, $CF_3$, $CH_3$, methoxy, hydroxyl and NR(20)R(21);
R(20) and R(21) independently of one another are H or ($C_1$–$C_4$)alkyl;
l is zero, 1 or 2;

or

R2 and R3
independently of one another are $SO_n$-R22;
n is zero, 1 or 2;
R22 is alkyl having 1, 2, 3, 4, 5, 6, 7 or 8 carbon atoms, cycloalkyl having 3, 4, 5, 6 or 7 carbon atoms or —$C_sH_{2s}$-phenyl,
said —$C_sH_{2s}$-phenyl being unsubstituted or substituted by 1–3 substituents selected from F, Cl, Br, I, $CF_3$, methyl, methoxy, hydroxyl and NR(34)R(35);
R(34) and R(35) independently of one another are H or ($C_1$–$C_4$)-alkyl;
s is zero, 1 or 2;

R4 and R5 independently of one another are hydrogen, alkyl having 1, 2, 3, 4, 5, 6, 7 or 8 carbon atoms, F, Cl, Br, I, $CF_3$, —C≡N, —$NO_2$, $SO_p$-R16, CO-R23 or O-R24;
p is zero, 1 or 2;
R16 is alkyl having 1, 2, 3, 4, 5, 6, 7 or 8 carbon atoms or phenyl,
said phenyl being unsubstituted or substituted by 1–3 substituents selected from F, Cl, Br, I, $CF_3$, methyl, methoxy, hydroxyl and NR(26)R(27);
R(26) and R(27) independently of one another are H or ($C_1$–$C_4$)-alkyl;
R23 is hydrogen, alkyl having 1, 2, 3, 4, 5, 6, 7 or 8 carbon atoms or OR25;
R25 is hydrogen, alkyl having 1, 2, 3, 4, 5, 6, 7 or 8 carbon atoms;
R24 is hydrogen, alkyl having 1, 2, 3, 4, 5, 6, 7 or 8 carbon atoms or phenyl,
said phenyl being unsubstituted or substituted by 1–3 substituents selected from F, Cl, Br, I, $CF_3$, methyl, methoxy, hydroxyl and NR(28)R(29);

R(28) and R(29) independently of one another are H or ($C_1$–$C_4$)-alkyl;

and their physiologically tolerable salts.

Preferred compounds of the formula I are those in which:

R1 is hydrogen, alkyl having 1, 2, 3 or 4 carbon atoms or —$C_aH_{2a}$-phenyl, said —$C_aH_{2a}$-phenyl being unsubstituted or substituted by 1–2 substituents selected from F, Cl, Br, $CF_3$, methyl, methoxy, hydroxyl and NR(8)R(9);

R(8) and R(9) independently of one another are H or methyl;

a is zero or 1;

or

R1 is ($C_1$–$C_9$)heteroaryl, which is unsubstituted or substituted by one substituent selected from F, Cl, Br, $CF_3$, $CH_3$, methoxy, hydroxyl and NR(10)R(11);

R(10) and R(11) independently of one another are H or methyl;

or

R1 is —$C_dH_{2d}$—($C_3$–$C_7$)cycloalkyl;

d is zero or 1;

R2 and R3 independently of one another are hydrogen, F, Cl, Br, $CF_3$, —C≡N, —$NO_2$, $CH_2OR17$, CO-R6 or O-R7;

R17 is hydrogen or alkyl having 1,2,3 or 4 carbon atoms;

R6 is hydrogen, alkyl having 1, 2, 3 or 4 carbon atoms, OR30 or phenyl, said phenyl being unsubstituted or substituted by 1–2 substituents selected from F, Cl, Br, $CF_3$, methyl, methoxy, hydroxyl and NR(31)R(32);

R(31) and R(32) independently of one another are H or methyl;

R30 is hydrogen or alkyl having 1, 2, 3 or 4 carbon atoms;

R7 is hydrogen, alkyl having 1, 2, 3 or 4 carbon atoms or phenyl, said phenyl being unsubstituted or substituted by 1–2 substituents selected from F, Cl, Br, $CF_3$, methyl, methoxy, hydroxyl and NR(12)R(13);

R(12) and R(13) independently of one another are H or methyl;

or

R7 is ($C_1$–$C_9$)heteroaryl, which is unsubstituted or substituted by one substituent selected from F, Cl, Br, $CF_3$, $CH_3$, methoxy, hydroxyl and NR(14)R(15);

R(14) and R(15) independently of one another are H or methyl;

or

R2 and R3 independently of one another are alkyl having 1, 2, 3 or 4 carbon atoms, cycloalkyl having 3, 4, 5, 6 or 7 carbon atoms or —$C_gH_{2g}$-phenyl, said —$C_gH_{2g}$-phenyl being unsubstituted or substituted by 1–2 substituents selected from F, Cl, Br, $CF_3$, methyl, methoxy, hydroxyl and NR(18)R(19);

R(18) and R(19) independently of one another are H or methyl;

g is zero or 1;

or

R2 and R3 independently of one another are ($C_1$–$C_9$)heteroaryl, which is unsubstituted or substituted by one substituent selected from F, Cl, Br, $CF_3$, $CH_3$, methoxy, hydroxyl and NR(20)R(21);

R(20) and R(21) independently of one another are H or methyl;

or

R2 and R3 independently of one another are $SO_n$-R22, n is zero, 1 or 2;

R22 is alkyl having 1, 2, 3 or 4 carbon atoms, cycloalkyl having 3, 4, 5, 6 or 7 carbon atoms or —$C_sH_{2s}$-phenyl, said —$C_sH_{2s}$-phenyl being unsubstituted or substituted by 1–2 substituents selected from F, Cl, Br, $CF_3$, methyl, methoxy, hydroxyl and NR(34)R(35);

R(34) and R(35) selected from H and methyl;

s is zero or 1;

R4 and R5 independently of one another are hydrogen, alkyl having 1, 2, 3 or 4 carbon atoms, F, Cl, Br, $CF_3$, —C≡N, —$NO_2$, $SO_p$—R16, CO-R23 or O-R24;

p is zero, 1 or 2;

R16 is alkyl having 1, 2, 3 or 4 carbon atoms or phenyl, said phenyl being unsubstituted or substituted by 1–2 substituents selected from F, Cl, Br, $CF_3$, methyl, methoxy, hydroxyl and NR(26)R(27);

R(26) and R(27) independently of one another are H or methyl;

R23 is hydrogen, alkyl having 1, 2, 3 or 4 carbon atoms or OR25; R25 is hydrogen or alkyl having 1, 2, 3 or 4 carbon atoms;

R24 is hydrogen, alkyl having 1, 2, 3 or 4 carbon atoms or phenyl, said phenyl being unsubstituted or substituted by 12–2 substituents selected from F. Cl Br, $CF_3$, methyl, methoxy, hydroxyl and NR(28)R(29);

R(28) and R(29) independently of one another are H or methyl;

and their physiologically tolerable salts.

Particularly preferred compounds of the formula I are those in which:

R1 is hydrogen, alkyl having 1, 2, 3 or 4 carbon atoms or phenyl, said phenyl being unsubstituted or substituted by one substituent selected from F, Cl, Br, $CF_3$, methyl, methoxy, hydroxyl and NR(8)R(9);

R(8) and R(9) independently of one another are H or methyl;

or

R1 is ($C_1$–$C_9$)heteroaryl, which is unsubstituted or substituted by one substituent selected from F, Cl, Br, $CF_3$, $CH_3$, methoxy, hydroxyl and NR(10)R(11);

R(10) and R(11) independently of one another are H or methyl;

or

R1 is ($C_3$–$C_7$)cycloalkyl;

R2 and R3 independently of one another are hydrogen, F, Cl, Br, $CF_3$, —C≡N, —$NO_2$, CO-R6 or O-R7;

R6 is hydrogen, alkyl having 1, 2, 3 or 4 carbon atoms, OR30 or phenyl, said phenyl being unsubstituted or substituted by one substituent selected from F, Cl, Br, $CF_3$, methyl, methoxy, hydroxyl and NR(31)R(32);

R(31) and R(32) independently of one another are H or methyl;

R30 is hydrogen or alkyl having 1, 2 or 3 carbon atoms

R7 is hydrogen, alkyl having 1, 2, 3 or 4 carbon atoms or phenyl, said phenyl being unsubstituted or substituted by one substituent selected from F, Cl, Br, $CF_3$, methyl, methoxy, hydroxyl and NR(12)R(13);

R(12) and R(13) independently of one another are H or methyl;

or

R7 is $(C_1-C_9)$heteroaryl, which is unsubstituted or substituted by one substituent selected from F, Cl, Br, $CF_3$, $CH_3$, methoxy, hydroxyl and NR(14)R(15); R4) and R(15) independently of one another are H or methyl;

or

R2 and R3 independently of one another are alkyl having 1, 2, 3 or 4 carbon atoms, cycloalkyl having 3, 4, 5, 6 or 7 carbon atoms or phenyl, said phenyl being unsubstituted or substituted by one substituent selected from F, Cl, Br, $CF_3$, methyl, methoxy, hydroxyl and NR(18)R(19);

R(18) and R(19) independently of one another are H or methyl;

or

R2 and R3 independently of one another are $(C_1-C_9)$heteroaryl, which is unsubstituted or substituted by one substituent selected from F, Cl, Br, $CF_3$, $CH_3$, methoxy, hydroxyl and NR(20)R(21);

R(20) and R(21) independently of one another are H or methyl;

or

R2 and R3 independently of one another are $SO_n$-R22;

n is zero or 2;

R22 is alkyl having 1, 2, 3 or 4 carbon atoms, cycloalkyl having 3, 4, 5, 6 or 7 carbon atoms or phenyl, said phenyl being unsubstituted or substituted by 1–2 substituents selected from F, Cl, Br, $CF_3$, methyl, methoxy, hydroxyl and NR(34)R(35);

R(34) and R(35) independently of one another are H or methyl;

$R^4$ and $R^5$ independently of one another are hydrogen, alkyl having 1, 2, 3 or 4 carbon atoms, F, Cl, $CF_3$, —CON, —$NO_2$, $SO_p$-R16, CO-R23 or O-R24;

p is zero or 2;

R23 is hydrogen, alkyl having 1, 2, 3 or 4 carbon atoms or OR25;

R25 is hydrogen or alkyl having 1, 2 or 3 carbon atoms;

R24 is hydrogen, alkyl having 1, 2, 3 or 4 carbon atoms or phenyl, said phenyl being unsubstituted or substituted by one substituent selected from F, Cl, Br, $CF_3$, methyl, methoxy, hydroxyl and NR(28)R(29);

R(28) and R(29) independently of one another are H or methyl;

R1 6 is alkyl having 1, 2, 3 or 4 carbon atoms or phenyl, said phenyl being unsubstituted or substituted by one substituent selected from F, Cl, Br, $CF_3$, methyl, methoxy, hydroxyl and NR(26)R(27);

R(26) and R(27) independently of one another are H or methyl;

and their physiologically tolerable salts.

Very particularly preferred compounds of the formula I are those in which:

R1 is alkyl having 1, 2, 3 or 4 carbon atoms or phenyl, said phenyl being unsubstituted or substituted by one substituent selected from F, Cl, $CF_3$, methyl and methoxy;

or

R1 is $(C_1-C_9)$heteroaryl, which is unsubstituted or substituted by one substituent selected from F, Cl, $CF_3$, $CH_3$ and methoxy;

or

R1 is $(C_3-C_7)$cycloalkyl;

R2 and R3 independently of one another are hydrogen, F, Cl, $CF_3$, —C≡N, CO-R6 or O-R7;

R6 is hydrogen, alkyl having 1, 2, 3 or 4 carbon atoms, OR30 or phenyl, said phenyl being unsubstituted or substituted by one substituent selected from F, Cl, $CF_3$, methyl and methoxy;

R30 is hydrogen, methyl or ethyl;

R7 is hydrogen, alkyl having 1, 2, 3 or 4 carbon atoms or phenyl, said phenyl being unsubstituted or substituted by one substituent selected from F, Cl, $CF_3$, methyl and methoxy;

or

R7 is $(C_1-C_9)$heteroaryl, which is unsubstituted or substituted by one substituent selected from F, Cl, Br, $CF_3$, $CH_3$ and methoxy;

or

R2 and R3 independently of one another are alkyl having 1, 2, 3 or 4 carbon atoms, cycloalkyl having 3, 4, 5, 6 or 7 carbon atoms or phenyl, said phenyl being unsubstituted or substituted by one substituent selected from F, Cl, $CF_3$, methyl and methoxy;

or

R2 and R3 independently of one another are $(C_1-C_9)$heteroaryl, which is unsubstituted or substituted by one substituent selected from F, Cl, $CF_3$, $CH_3$ and methoxy;

or

R2 and R3 independently of one another are $SO_n$-R22;

n is zero or 2;

R22 is alkyl having 1, 2, 3 or 4 carbon atoms or phenyl, said phenyl being unsubstituted or substituted by 1–2 substituents selected from F, Cl, $CF_3$, methyl and methoxy;

R4 and R5 independently of one another are hydrogen, methyl, F, Cl, $CF_3$, —C≡N, $SO_2$-R16, CO-R23 or O-R24;

$R^{16}$ is alkyl having 1, 2, 3 or 4 carbon atoms or phenyl, said phenyl being unsubstituted or substituted by one substituent selected from F, Cl, $CF_3$, methyl and methoxy;

R23 is hydrogen, methyl or OR25; R25 is hydrogen, methyl or ethyl;

R24 is hydrogen, alkyl having 1, 2, 3 or 4 carbon atoms or phenyl,
  said phenyl being unsubstituted or substituted by one substituent selected from F. Cl, CF₃, methyl and methoxy;

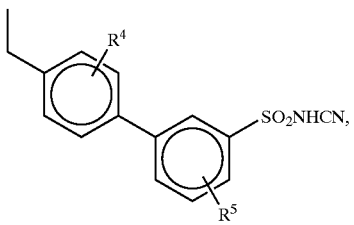
Ia

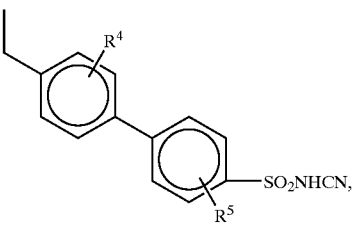
Ib

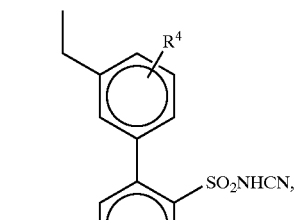
Ic

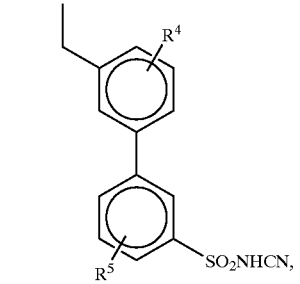
Id

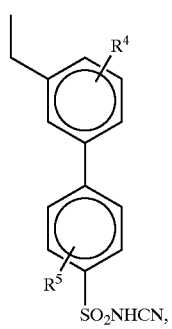
Ie

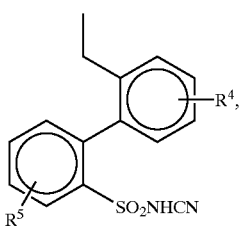
If

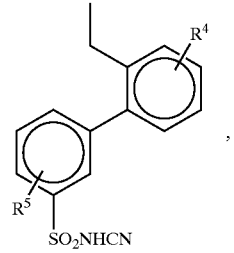
Ig

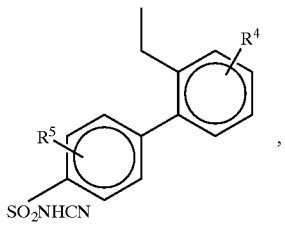
Ih and their physiologically tolerable salts.

In addition, preferred compounds of the formula I are those in which the radicals $R1_1$, R2, R3, R4 and R5 are as defined above, where $R^4$ and $R^5$ are not simultaneously hydrogen.

Alkyl can be straight-chain or branched.

Cycloalkyl is also understood as meaning alkyl-substituted rings. $(C_1-C_9)$Heteroaryl is understood as meaning in particular radicals which are derived from phenyl or naphthyl, in which one or more CH groups are replaced by N and/or in which at least two adjacent CH groups (with formation of a five-membered aromatic ring) are replaced by S, NH or O. In addition, one or both atoms of the condensation site of bicyclic radicals (such as indolizinyl) can also be nitrogen atoms.

Heteroaryl is in particular furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl.

Stereocenters which may occur can have either the (R) or the (S) configuration.

Physiologically tolerable salts of compounds of the formula I are understood as being both their organic and inorganic salts, such as are described in Remington's Pharmaceutical Sciences [17th Edition, page 1418 (1985)]. On account of the physical and chemical stability and the solubility, for acidic groups, inter alia, sodium, potassium, calcium and ammonium salts are preferred; for basic groups, inter alia, salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid, are preferred.

The invention also relates to a process for the preparation of the compounds of the formula I, and their physiologically tolerable salts, which comprises reacting a compound of the formula II

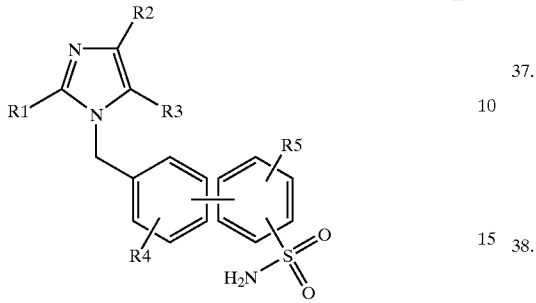

II in which the radicals are as defined above and which are either known from J. Med. Chem. 1995, 38, 2357 or were prepared analogously, with cyanogen bromide. The reaction is carried out in a dipolar aprotic solvent which is stable to cyanogen bromide, for example acetonitrile, DMA, TMU or NMP, using a strong auxiliary base which is not very nucleophilic, such as, for example, $K_2CO_3$ or $Cs_2CO_3$. A suitable reaction temperature is a temperature from 0° C. to the boiling point of the solvent used; a temperature from 60° C. to 120 C. is preferred.

The invention furthermore relates to the use of a compound of the formula

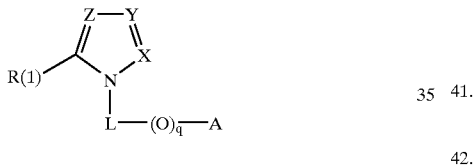

in which:
a) X, Y and Z are, identically or differently, N or CR(102)
b) R(1) is
1. $(C_1-C_{10})$alkyl, 2. $(C_3-C_{10})$alkenyl, 3. $(C_3-C_{10})$alkynyl, 4. —OR(103), 5. $(C_3-C_8)$cycloalkyl, 6. $(C_4-C_{10})$cycloalkylalkyl, 7. $(C_5-C_{10})$-cycloalkylalkenyl, 8. $(C_5-C_{10})$cycloalkylalkynyl, 9. —$(CH_2)_m$—B—$(CH_2)_n$—R(104), 10. -benzyl, 11. a radical defined as under b) 1., 2., 3. or 9., which is monosubstituted by $CO_2R(103)$, 12. a radical as defined under b) 1., 2., 3. or 9., in which 1 to all hydrogen atoms are substituted by fluorine, or 13. the radical defined under b) 10., which is substituted on the phenyl by 1 or 2 identical or different radicals from halogen, $(C_1-C_4)$alkoxy and nitro,
c) R(102) is
1. hydrogen, 2. halogen, 3. nitro, 4. $C_vF_{2v+1}$, 5. pentafluorophenyl, 6. cyano, 7. —O—R(106), 8. phenyl, 9. phenyl$(C_1-C_3)$alkyl, 10. $(C_1-C_{10})$alkyl, 11. $(C_3-C_{10})$alkenyl, 12. phenyl$(C_2-C_6)$alkenyl, 13. 1-imidazolyl$(CH_2)_m$—, 14. 1,2,3-triazolyl$(CH_2)_n$—, 15. tetrazolyl$(CH_2)_m$—, 16. —$(CH_2)_{0-1}$—R(107)—OR(105), 17. —$(CH_2)_o$—O—CO—R(103), 18. —$(CH_2)_o$—S—R(106), 19. —S(O)$_r$—R(119), 20. —CH=CH—$(CH_2)_m$—CHR(103)—OR(106), 21. —CH=CH—$(CH_2)_m$—CO—R(108), 22. —CO—R(108), 23. —CH=CH—$(CH_2)_m$—O—CO—R(107), 24. —$(CH_2)_m$—CH($CH_3$)—CO—R(108), 25. —$(CH_2)_o$—CO—R(108), 26. —$(CH_2)_o$—O—[C=W]—NH—R(109), 27. —$(CH_2)_o$—NR(107)—[C=W]—OR(109), 28. —$(CH_2)_o$—NR(107)—CO—NHR(109), 29. —$(CH_2)_o$NR(107)—$SO_2R(109)$, 30. —$(CH_2)_o$—NR(107)—[C=W]—R(109), 31. —$(CH_2)_n$F, 32. —$(CH_2)_n$—O—$NO_2$, 33. —$CH_2$—$N_3$, 34. —$(CH_2)_n$—$NO_2$, 35. —CH≡N—NR(105)R(107), 36. phthalimido$(CH_2)_n$—,

37.

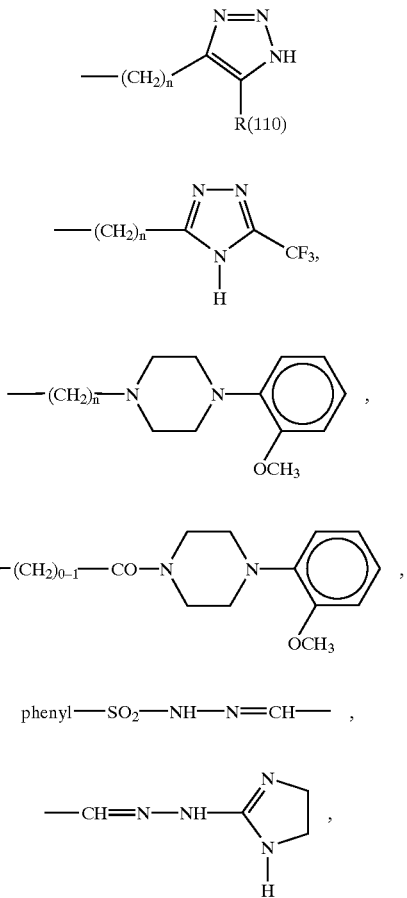

43. —$(CH_2)_n$—$SO_2$—NR(107)—CS—NR(106)R(109), 44. —$(CH_2)_n$—$SO_2$—NR(107)—CO—NR(106)R(109), 45. —$(CH_2)_o$—$SO_2R(109)$, 46. a radical as defined under c) 8. or 9., which is substituted on the phenyl by 1 or 2 identical or different radicals from halogen, hydroxyl, methoxy, trifluoromethyl, $CO_2R(103)$ and phenyl, 47. a radical as defined under c) 10., 11. or 19., in which one to all hydrogen atoms are substituted by fluorine, 48. the radical defined under c) 14., which is substituted by 1 or 2 identical or different radicals from methoxycarbonyl and $(C_1-C_4)$alkyl, 49. —$(CH_2)_n$—$SO_2$—NR(107)—CO—R(106), 50. —$(CH_2)_n$—$SO_2$—NR(107)CS—R(106),
d) R(103) is
1. hydrogen, 2. $(C_1-C_8)$alkyl, 3. $(C_3-C_8)$cycloalkyl, 4. phenyl, 10 5. benzyl, 6. the radical defined under d) 2., in which 1 to all H atoms are substituted by fluorine;
e) R(104) is 1. hydrogen, 2. $(C_1-C_6)$alkyl, 3. $(C_3-C_8)$cycloalkyl, 4. $(C_2-C_4)$-alkenyl or 5. $(C_2-C_4)$alkynyl;
f) R(105) is 1. hydrogen, 2. $(C_1-C_6)$alkyl, 3. $(C_3-C_8)$cycloalkyl, 4. phenyl or 5. benzyl;

g) R(106) and R(109) are, identically or differently, 1. hydrogen, 2. ($C_1$–$C_6$)alkyl which is unsubstituted or substituted by 1–3 substituents selected from ($C_1$–$C_6$) alkoxy which for its part can be substituted by 1–3 radicals from hydroxyl, ($C_1$–$C_6$)alkoxy, amino, mono-($C_1$–$C_6$)alkylamino, di($C_1$–$C_6$)alkylamino, ($C_2$–$C_{10}$) alkenyl, hydroxyl, amino, mono-($C_1$–$C_6$)alkylamino, di($C_1$–$C_6$)alkylamino, ($C_1$–$C_6$)-alkoxycarbonylamino, ($C_6$–$C_{12}$)aryl($C_1$–$C_4$)alkoxycarbonylamino, ($C_6$–$C_{10}$) aryl, ($C_6$–$C_{10}$)aryl($C_1$–$C_3$)alkyl, ($C_1$–$C_3$)heteroaryl, carboxyl and ($C_1$–$C_4$)alkoxycarbonyl; 3. ($C_3$–$C_8$) cycloalkyl, where the cycloalkyl moiety is unsubstituted or substituted by 1–3 substituents selected from ($C_1$–$C_4$)alkyl and ($C_2$–$C_4$)alkenyl; 4. ($C_3$–$C_8$)cycloalkyl($C_1$–$C_3$) alkyl, 5. ($C_6$–$C_{12}$)aryl, preferably phenyl, 6. ($C_6$–$C_{10}$)aryl($C_1$–$C_4$)alkyl, 7. ($C_1$–$C_9$)heteroaryl, which can be partially or completely hydrogenated, 8. a radical defined as under g) 5., 6., 7., 9., 15., 16., 17., 19., 20. or 21., substituted by 1 or 2 identical or different radicals selected from halogen, hydroxyl, ($C_1$–$C_4$)alkyl, methoxy, nitro, cyano, $CO_2R(103)$, trifluoromethyl, NR(111)R(112) and

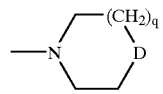

9. ($C_1$–$C_9$)heteroaryl($C_1$–$C_3$)alkyl,
where the heteroaryl moiety can be partially or completely hydrogenated, 10. ($C_1$–$C_6$)alkyl, in which 1 to all H atoms are substituted by fluorine, 11. ($C_2$–$C_{10}$)alkenyl, ($C_2$–$C_{10}$)-alkenoyl or ($C_2$–$C_{10}$) alkadienyl, 12. ($C_3$–$C_8$)cycloalkenyl, 13. ($C_3$–$C_8$) cycloalkenyl($C_1$–$C_3$)alkyl, 14. bi- or tricyclic ($C_4$–$C$ )cycloalkenyl($C_1$–$C_4$)alkyl, which can also be substituted by 1–3 ($C_1$–$C_4$)-alkyl radicals;

15. ($C_6$–$C_{10}$)aryl($C_1$–$C_4$)alkyl, 16. ($C_6$–$C_{10}$)aryl ($C_3$–$C_6$)-alkenyl, 17. ($C_1$–$C_9$)heteroaryl($C_3$–$C_6$) alkenyl, 18. ($C_3$–$C_6$)alkynyl, 19. ($C_6$–$C_{10}$)aryl ($C_3$–$C_6$)alkynyl, 20. ($C_1$–$C_9$)heteroaryl($C_3$–$C_6$) alkynyl, 21. R(106) and R(109) together with the nitrogen atom carrying them are a heteroaryl, which can also be partially or completely hydrogenated;

h) R(107) is
1. hydrogen, 2. ($C_1$–$C_6$)alkyl, 3. ($C_3$–$C_8$)cycloalkyl, 4. ($C_6$–$C_{12}$)-aryl($C_1$–$C_6$)alkyl, preferably benzyl, 5. phenyl or 6. ($C_1$–$C_9$)-heteroaryl;

i) R(108) is
1. hydrogen, 2. ($C_1$–$C_6$)alkyl, 3. ($C_3$–$C_8$)cycloalkyl, 4. phenyl-($CH_2$)$_q$—, 5. OR(106), 6. NR(111)R(112) or 7.

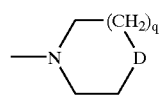

j) R(110) is
cyano, nitro or $CO_2R(107)$;

k) R(111) and R(112) are,
identically or differently, 1. hydrogen, 2. ($C_1$–$C_4$)alkyl, 3. phenyl, 4. benzyl, or 5. α-methylbenzyl;

l) D is NR(113), O or $CH_2$;

m) R(113) is
hydrogen, ($C_1$–$C_4$)alkyl or phenyl;

n) A is biphenylyl,
which is unsubstituted or substituted by 1–4, preferably 1 to 2, identical or different substituents R(114) or R(115);

o) R(114) is
1. halogen, 2. nitroso, 3. nitro, 4. amino, 5. cyano, 6. hydroxyl, 7. ($C_1$–$C_6$)alkyl, 8. ($C_1$–$C_4$)alkanoyl, 9. ($C_1$–$C_4$)-alkanoyloxy, 10. $CO_2R(103)$, 11. methanesulfonylamino, 12. trifluoromethanesulfonylamino, 13. —CO—NH—OR(109), 14. —$SO_2$—NR(106)R(107), 15. —$CH_2$—OR(107), 16. ($C_1$–$C_9$)-heteroaryl($CH_2$)$_q$—, preferably 1-tetrazolyl, 17. ($C_7$–$C_{13}$)aroyl, 18. 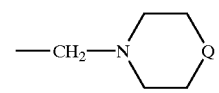

19. 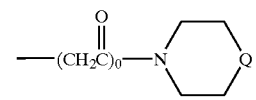

or 20. ($C_6$–$C_{12}$)aryl;

p) R(115) is
1. hydrogen, 2. ($C_1$–$C_6$)alkyl, 3. ($C_3$–$C_8$)cycloalkyl, 4. ($C_6$–$C_{12}$)-aryl, 5. ($C_7$–$C_{13}$)aroyl, 6. ($C_1$–$C_4$)alkoxy, 7. ($C_1$–$C_4$)-alkanoyloxy, 8. ($C_1$–$C_9$)heteroaryl, 9. $CO_2R(103)$, 10. halogen, 11. cyano, 12. nitro, 13. NR(106)R(107), 14. hydroxyl, 15. —CO—NH—CHR(105)—$CO_2R(103)$, 16. sulfo, 17. —$SO_3R$ (103), 18. —$SO_2$—NR(107)—CO—NR(106)R (109) or —$SO_2$—NR(107)—CS—NR(106)R(109), 19. —NR(107)—CO—NR(106)—$SO_2$—$CH_2$-R (105), 20. —C($CF_3$)$_2$OH, 21. phosphonooxy, 22. —$PO_3H_2$, 23. —NH—PO(OH)$_2$, 24. —S(O)$_r$R (106), 25. —CO—R(108), 26. —CO—NR(106)R (109), 27. —CR(120)(OH)—PO(OH)$_2$, 28. the radical defined under o) 20., 29. 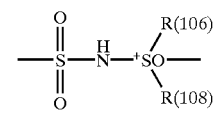

30. 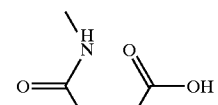

31. 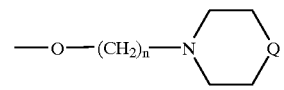

32. 5-tetrazolyl-NH—CO—, 33. —CO—NH—NH—$SO_2$—$CF_3$,

34. 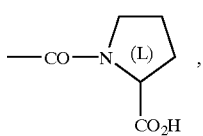

35. 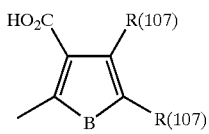

36. 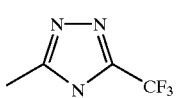

37. 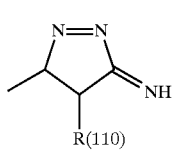

38. 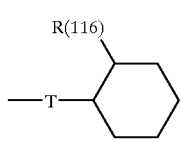

39. 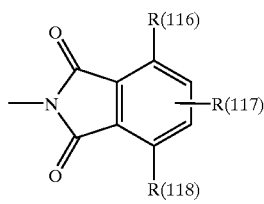

40. —CO—NH—SO$_2$-R(119), 41. —SO$_2$—NH—CO—R(106) or 42. the radical defined under p) 4., substituted by 1 or 2 identical or different radicals selected from halogen, cyano, nitro, NR(106)R(107) and hydroxyl; 43. R(115) together with R(114) is —CO—NH—SO$_2$—, 44. —SO$_2$—NH—CO—O-R(106), 45. —SO$_2$—NH—SO$_2$—NR(106)R(109), 46. —SO$_2$—NH—SO$_2$-R(106);

q) B is O, NR(107) or S;
r) W is O or S;
s) L is (C$_1$–C$_3$)alkanediyl;
t) R(116) is CO$_2$R(103) or CH$_2$CO$_2$R(103);
u) R(117) is hydrogen, halogen, (C$_1$–C$_4$)alkyl or (C$_1$–C$_4$) alkoxy;
v) R(118) is hydrogen, (C$_1$–C$_4$)alkyl or phenyl;
w) R(119) is 1. (C$_1$–C$_6$)alkyl, 2. (C$_3$–C$_8$)cycloalkyl, 3. phenyl, 4. benzyl or 5. the radical defined under w) 1., in which one to all H atoms are substituted by fluorine,
x) T is 1. a single bond, 2. —CO—, 3. —CH$_2$—, 4. —O—, 5. —S—, 6. —NR(121)—, 7. —CO—NR(121), 8. —NR(121)—CO—, 9. —O—CH$_2$—, 10. —Cl$_2$—, O—, 11. —S—CH$_2$—, 12. —CH$_2$—S, 13. —NH—CR(120)R(122), 14. —NR(121)—SO$_2$, 15. SO$_2$—NR(121)—, 16. —CR(120)R(122)—NH, 17. —CH=CH—, 18. —CF=CF—, 19. —CH=CF—, 20. —CF=CH—, 21. —CH$_2$—CH$_2$—, 22. —CF$_2$—CF$_2$—, 23. —CH[OR(103)]—, 24. —CH(OCOR(105))—, 25. —C[N=R(123)]— or 26. [R(124)O]—C—[OR(125)]— y) R(120) and R(122) are, identically or differently, hydrogen, (C$_1$–C$_5$)alkyl, phenyl, allyl or benzyl;
z) R(121) is hydrogen, (C$_1$–C$_6$)alkyl, benzyl or allyl;
a') R(123) is 1. NR(120)R(121), 2. ureido, 3. thioureido, 4. toluene-4-sulfonyl or 5. benzenesulfonylamino;
b') R(124) and R(125) are, identically or differently, (C$_1$–C$_4$)alkyl or together —(CH$_2$)$_q$;
c') Q is CH$_2$, NH, O or S;
d') m is 1, 2, 3, 4 or 5;
e') n is 1, 2, 3, 4 or 5;
f') o is 1, 2, 3, 4, 5, 6, 7, 8, 9 or 10;
g') q is zero or 1;
h') r is zero, 1 or 2;
i') v is 1, 2, 3, 4, 5 or 6;

and of their physiologically tolerable salts for the production of a medicament for the treatment or prophylaxis of illnesses caused by ischemic conditions, and also for the production of a medicament for the treatment of impaired respiratory drive.

In addition, the invention relates to the use of a compound of the formula I for the production of a medicament for the treatment or prophylaxis of illnesses caused by ischemic conditions;

and also the use of a compound of the formula I for the production of a medicament for the treatment or prophylaxis of cardiac infarct;

and also the use of a compound of the formula I for the production of a medicament for the treatment or prophylaxis of angina pectoris;

and also the use of a compound of the formula I for the production of a medicament for the treatment or prophylaxis of ischemic conditions of the heart:

and also the use of a compound of the formula I for the production of a medicament for the treatment or prophylaxis of ischemic conditions of the peripheral and central nervous system and of stroke;

and also the use of a compound of the formula I for the production of a medicament for the treatment or prophylaxis of ischemic conditions of peripheral organs and members;

and the use of a compound of the formula I for the production of a medicament for the treatment of states of shock;

and also the use of a compound of the formula I for the production of a medicament for use in surgical operations and organ transplantation;

and also the use of a compound of the formula I for the production of a medicament for the preservation and storage of transplants for surgical measures;

and also the use of a compound of the formula I for the production of a medicament for the treatment of illnesses in which cell proliferation is a primary or secondary cause; and thus their use for the production of an antiatherosclerotic or a composition against diabetic late complications, carcinomatous disorders, fibrotic disorders such as pulmonary fibrosis, hepatic fibrosis or renal fibrosis, or prostate hyperplasia;

and also the use of a compound of the formula I for the production of a medicament for the treatment of impaired respiratory drive;

and also a pharmaceutical which comprises an efficacious amount of a compound of the formula I.

Compounds similar to the compounds of the formula I according to the invention are disclosed in U.S. Pat. Nos. 5,482,957 and 5,604,251. However, they do not have the sulfonylcyanamide side chain always present according to the invention. Imidazole derivatives as angiotensin 11 antagonists are also described in WO9523792, WO9523791, U.S. Pat. No. 5,391,732, EP-A 648763. In addition, in U.S. Pat. No. 5,281,614, triazole derivatives and, in WO 9220662 and in J. Med. Chem. (1994), 37 (17), 2808–2824, triazolinone derivatives are described as angiotensin 11 receptor antagonists. The known compounds are angiotensin II receptor antagonists of the subtype AT1, which action is not present or is only present to a small extent in the compounds I according to the invention.

The compounds of the formula I according to the invention exhibit very good antiarrhythmic properties, such as are important, for example, for the treatment of illnesses which occur in the case of oxygen deficiency symptoms. Because of their pharmacological properties, the compounds of the formula I are outstandingly suitable as antiarrhythmic pharmaceuticals having a cardioprotective component for infarct prophylaxis and infarct treatment and also for the treatment of angina pectoris, where they also preventively inhibit or greatly decrease the pathophysiological processes in the formation of ischemically induced damage, in particular in the elicitation of ischemically induced cardiac arrhythmias.

Because of their protective actions against pathological hypoxic and ischemic situations, the compounds of the formula I according to the invention can be used, as a result of inhibition of the cellular $Na^+$-dependent $Cl^-/HCO_3^-$ exchange mechanism or of the sodium/bicarbonate symporter, as a pharmaceutical for the treatment of all acute or chronic damage caused by ischemia or illnesses induced primarily or secondarily thereby. They protect organs which are acutely or chronically undersupplied with oxygen by reducing or preventing ischemically induced damage and are thus suitable as pharmaceuticals, for example in thrombosis, vasospasms, atherosclerosis or in surgical interventions (e.g. in kidney and liver organ transplantation, where the compounds can be used both for the protection of the organs in the donor before and during removal, for the protection of removed organs, for example during treatment with or storage thereof in physiological bath fluids, and in the transfer to the recipient's body) or acute kidney failure. The compounds of the formula I are also valuable pharmaceuticals having a protective action when carrying out angioplastic surgical interventions, for example on the heart and also on peripheral vessels. Corresponding to their protective action against ischemically induced damage, the compounds are also suitable as pharmaceuticals for the treatment of ischemias of the nervous system, in particular of the central nervous system, where they are suitable, for example, for the treatment of stroke or of cerebral edema. Moreover, the compounds of the formula I according to the invention are also suitable for the treatment of forms of shock, such as, for example, of allergic, cardiogenic, hypovolemic and of bacterial shock.

Moreover, the compounds of the formula I according to the invention are distinguished by strong inhibitory action on the proliferation of cells, for example fibroblast cell proliferation and the proliferation of the vascular smooth muscle cells. Therefore the compounds of the formula I are suitable as valuable therapeutics for illnesses in which cell proliferation is a primary or secondary cause, and can therefore be used as antiatherosclerotics, agents against diabetic late complications, carcinomatous disorders, fibrotic disorders such as pulmonary fibrosis, hepatic fibrosis or renal fibrosis, organ hypertrophies and hyperplasias, in particular in prostate hyperplasia or prostate hypertrophy.

It was found that inhibitors of the $Na^+$-dependent $Cl^-/HCO_3^-$ exchanger or of the sodium/bicarbonate symporter can stimulate the respiration by an increase in the chemosensitivity of the respiratory chemoreceptors. These chemoreceptors are responsible to a considerable extent for the maintenance of an ordered respiratory activity. They are activated by hypoxia, pH decrease and rise in $CO_2$ (hypercapnia) in the body and lead to an adjustment of the respiratory minute volume. During sleep, the respiration is particularly susceptible to disturbance and is dependent to a great extent on the activity of the chemoreceptors.

Improvement in the respiratory drive by stimulation of the chemoreceptors with substances which inhibit $Na^+$-dependent $Cl^-/HCO_3^-$ exchange leads to an improvement in the respiration in the following clinical conditions and illnesses: disturbed central respiratory drive (e.g. central sleep apnea, cot death, postoperative hypoxia), muscle-related respiratory disorders, respiratory disorders after long-term ventilation, respiratory disorders during adaptation in a high mountain region, obstructive and mixed forms of sleep apneas, acute and chronic lung diseases with hypoxia and hypercapnia.

Pharmaceuticals which contain a compound of the formula I can in this case be administered orally, parenterally, intravenously, rectally or by inhalation, the preferred manner of administration being dependent on the particular symptoms of the disorder. The compounds of the formula I can in this case be used on their own or together with pharmaceutical auxiliaries, namely both in veterinary and in human medicine.

Auxiliaries which are suitable for the desired pharmaceutical formulation are familar to the person skilled in the art on the basis of his expert knowledge. Beside solvents, gel-forming agents, suppository bases, tablet auxiliaries, and other vehicles, it is possible to use, for example, antioxidants, dispersants, emulsifiers, antifoams, flavor corrigents, preservatives, solubilizers or colorants.

For an oral administration form, the active compounds are mixed with the additives suitable therefor, such as excipients, stabilizers or inert diluents, and brought by the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. In this case preparation can be carried out both as dry and as moist granules. Suitable oily excipients or solvents are, for example, vegetable or animal oils, such as sunflower oil or cod liver oil.

For subcutaneous or intravenous administration, the active compounds, if desired with the substances customary therefor such as solubilizers, emulsifiers or further auxiliaries, are brought into solution, suspension or emulsion. Possible solvents are, for example: water, physiological saline solution or alcohols, e.g. ethanol, propanol, glycerol, and in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also contain other pharmaceutical auxiliaries such as surfactants, emulsifiers and stabilizers and also a propellant gas. Such a preparation contains the active compound customarily in a concentration from approximately 0.1 to 10, in particular from approximately 0.3 to 3, % by weight.

The dose of the active compound of the formula I to be administered and the frequency of administration depend on the potency and duration of action of the compounds used; additionally also on the nature and severity of the illness to be treated and on the sex, age, weight and individual responsiveness of the mammal to be treated.

On average, the daily dose of a compound of the formula I in the case of a patient weighing approximately 75 kg is at least 0.001 mg/kg, preferably 0.01 mg/kg, to at most 10 mg/kg, preferably 1 mg/kg, of body weight. In the case of acute episodes of the illness, for example immediately after suffering a cardiac infarct, higher and especially more frequent doses may also be necessary, e.g. up to 4 individual doses per day. In particular in the case of i.v. administration, for example in the case of an infarct patient in the intensive care unit, up to 200 mg per day may be necessary.

The compounds of the formula I can be employed as sole active compounds or in combination with other pharmacologically active compounds.

The compounds of the formula I and/or their physiologically tolerable salts can be employed to achieve an advantageous therapeutic action and, together with other pharmacologically active compounds, for the treatment or prophylaxis of the abovementioned symptoms, in particular for the treatment of cardiovascular disorders. Combination with inhibitors of the sodium/hydrogen exchanger (NHE) and/or with active substances from other classes of cardiovascular active compound is preferred.

The invention additionally relates very generally to the combination of a) NCBE inhibitors and/or their physiologically tolerable salts with NHE inhibitors and/or their physiologically tolerable salts; b) NCBE inhibitors and/or their physiologically tolerable salts with active substances from other classes of cardiovascular active compound and/or their physiologically tolerable salts and also c) of NCBE inhibitors and/or their physiologically tolerable salts with NHE inhibitors and/or their physiologically tolerable salts and with active substances from other classes of cardiovascular active compound and/or their physiologically tolerable salts. Preferred combinations are those in which NCBE inhibitors of the formula I and/or their physiologically tolerable salts are used.

The active compounds which are known and identified as NHE inhibitors are guanidine derivatives, preferably acylguanidine, inter alia such as are described in Edward J. Cragoe, Jr., "DIURETICS, Chemistry, Pharmacology and Medicine", J. WILEY & Sons (1983), 303–341 or the NHE inhibitors mentioned in DE19737224.4. The disclosures of both of these documents are specifically incorporated by reference herein.

Suitable NHE inhibitors are, for example, also benzoylguanidines such as are described in U.S. Pat. No. 5,292,755, U.S. Pat. No. 5,373,024, U.S. Pat. No. 5,364,868, U.S. Pat. No. 5,591,754, U.S. Pat. No. 5,516,805, U.S. Pat. No. 5,559,153, U.S. Pat. No. 5,571,842, U.S. Pat. No. 5,641,792, U.S. Pat. No. 5,631,293, EP-A 577024, EP-A 602522, EP-A 602523, EP-A 603650, EP-A 604852, EP-A 612723, EP-A 627413, EP-A 628543, EP-A 640593, EP-A 640588, EP-A 702001, EP-A 713864, EP-A 723956, EP-A 754680, EP-A 765868, EP-A 774459, EP-A 794171, DE 19624178.2, DE 19713427.0; ortho-substituted benzoylguanidines, such as are described in EP-A 556673, EP-A 791577, EP-A 794172, DE 19624178.2; ortho-amino-substituted benzoylguanidines, such as are described in EP-A 690048; isoquinolines, such as are described in EP-A 590455; benzo-fused 5-membered ring heterocycles, such as are described in EP-A 639573; diacyl-substituted guanidines, such as are described in EP-A 640587; acylguanidines, such as are described in U.S. Pat. No. 5,547,953; phenyl-substituted alkyl- or alkenylcarboxylic acids bearing perfluoroalkyl groups, such as are described in U.S. Pat. No. 5,567,734, EP-A 688766; heteroaroylguanidines, such as are described in EP-A 676395; bicyclic heteroaroylguanidines, such as are described in EP-A 682017; indenoylguanidines, such as are described in EP-A 738712; benzyloxycarbonylguanidines, such as are described in EP-A 748795; phenyl-substituted alkenylcarboxylic acid guanidines bearing fluorophenyl groups, such as are described in EP-A 744397; substituted cinnamoylguanidines, such as are described in EP-A 755919; sulfonimidamides, such as are described in EP-A 771788; benzenedicarboxylic acid diguanidines, such as described in EP-A 774458, EP-A 774457; diarylcarboxylic acid diguanidines, such as are described in EP-A 787717; substituted thiophenylalkenylcarboxylic acid guanidines, such as are described in EP-A 790245; bis-ortho-substituted benzoylguanidines, such as are described in DE 19621319.3; substituted 1- or 2-naphthylguanidines, such as are described in DE 19621482.3 and DE 19621483.1; indanylideneacetylguanidines, such as are described in EP 96112275.1; phenyl-substituted alkenylcarboxylic acid guanidines such as are described in DE 19633966.9; aminopiperidylbenzoylguanidines, such as are described in EP 667341; heterocycloxybenzylguanidines, such as are described in EP-A 694537; ortho-substituted benzoylguanidines, such as are described in EP704431; ortho-substituted alkylbenzylguanidines, such as are described in EP-A 699660; ortho-substituted heterocyclylbenzoylguanidines, such as are described in EP-A 699666; ortho-substituted 5-methylsulfonylbenzoylguanidines, such as are described in EP-A 708088; ortho-substituted 5-alkylsulfonylbenzoylguanidines having 4-amino substituents, such as are described in EP-A 723963; ortho-substituted 5-alkylsulfonylbenzoylguanidines having 4-mercapto substituents, such as are described in EP-A 743301; 4-sulfonyl- or 4-sulfinylbenzylguanidines, such as are described in EP-A 758644; alkenylbenzoylguanidines, such as are described in EP-A 760365; benzoylguanidines having fused, cyclic sulfones, such as are described in DE 19548708; benzoyl-, polycyclic aroyl- and heteroaroylguanidines, such as are described in WO 9426709; 3-aryl/heteroarylbenzoylguanidines, such as are described in WO 9604241; 3-phenylbenzoylguanidines having a basic amide in the 5-position, such as are described in WO 9725310; 3-dihalothienyl- or 3-dihalophenylbenzoylguanidines having a basic substituent in the 5-position, such as are described in WO 9727183; 3-methylsulfonylbenzoylguanidines having certain amino substituents in the 4-position, such as are described in WO 9512584; amiloride derivatives, such as are described in WO 9512592; 3-methylsulfonyl-benzoylguanidines having certain amino substituents in the 4-position, such as are described in WO 9726253; indoloylguanidines, such as are described in EP-A 622356 and EP-A 708091; indoloylguanidines having a fused additional ring system, such as are described in EP 787728; methylguanidine derivatives, such as are described in WO 9504052; 1,4- benzoxazinoylguanidines, such as are described in EP-A 719766; 5-bromo-2-naphthoylguanidines, such as are described in JP 8225513; quinoline-4-carbonylguanidines having a phenyl radical in the 2-position, such as are described in EP-A 726254; cinnamoylguanidines, such as are described in JP 09059245; propenoylguanidines having a naphthalene substituent, such as are described in JP 9067332; propenoylguanidines having indole substituents, such as are described in JP 9067340; or heteroaryl-substituted acryloylguanidines, such as are described in WO 9711055, and their physiologically tolerable salts. The disclosures of all of these documents are specifically incorporated by reference herein.

Preferred NHE inhibitors are the compounds emphasized as preferred in the publications mentioned. Very particularly preferred compounds are cariporide (HOE642), HOE 694, EMD 96785, FR 168888, FR 183998, SM-20550, KBR-9032, and their physiologically tolerable salts. Most preferred is cariporide or its physiologically tolerable salt.

Examples of classes of active compounds having cardiovascular activity which can be combined advantageously with NCBE inhibitors therapeutically or can additionally be combined with combinations of NCBE inhibitors and NHE inhibitors are beta-receptor blockers, calcium antagonists, angiotensin-converting enzyme inhibitors, angiotensin receptor blockers, loop diuretics, thiazide diuretics, potassium-sparing diuretics, aldosterone antagonists, such as are employed, for example, in lowering of the blood pressure, and also cardiac glycosides or other agents increasing the contractile force in the treatment of cardiac insufficiency and of congestive heart failures, and also antiarrhythmics of the classes I–IV, nitrates, $K_{ATP}$ openers, $K_{ATP}$ blockers, inhibitors of the veratridine-activatable sodium channel, etc. For example, the following are thus suitable: the beta-blockers propanolol, atenolol, metoprolol; the calcium antagonists diltiazem hydrochloride, verapamil hydrochloride, nifedipine; the ACE inhibitors captopril, enalapril, ramipril; trandolapril, quinapril, spirapril, preferably ramipril or trandolapril; the angiotensin II receptor antagonists losartan, valsartan, telmisartan, eprosartan, tasosartan, candesartan, irbesartan; the loop diuretics furosemide, piretanide, torasemide; the thiazide diuretics hydrochlorothiazide, metolazone, indapamide; the potassium-sparing diuretics amiloride, triamterene, spironolactone; the cardiac glycosides digoxin, digitoxin, strophanthin; the antiarrhythmics amiodarone, sotalol, bretylium, flecainide; the nitrate glycerol trinitrate; the $K^+$(ATP) openers cromakalim, lemakalim, nocorandil, pinacidil, minoxidil; the inhibitors of the veratridine-activatable Nat channel.

An example of such a particularly advantageous combination component with NCBE inhibitors are blockers of the non-inactivating sodium channel (veratridine-activatable sodium channel). The combinations of an NCBE inhibitor with a blocker of the non-inactivating sodium channel (veratridine-activatable sodium channel) are suitable for infarct and reinfarct prophylaxis and infarct treatment and also for the treatment of angina pectoris and the inhibition of ischemically induced cardiac arrhythmias, tachycardia and the formation and maintenance of ventricular fibrillation, the combinations of an NCBE inhibitor with a blocker of the non-inactivating sodium channel also preventively inhibiting or greatly decreasing the pathophysiological processes in the formation of ischemically induced damage. Because of their enhanced protective actions against pathological hypoxic and ischemic situations, the combinations according to the invention of an NCBE inhibitor with a blocker of the non-inactivating sodium channel are used, as a result of enhanced inhibition of the $Na^+$ influx into the cell, as pharmaceuticals for the treatment of all acute or chronic damage induced by ischemia or diseases induced primarily or secondarily thereby. This relates to their use as pharmaceuticals for surgical interventions, e.g. in organ transplantation, where the combinations of an NCBE inhibitor with a blocker of the non-inactivating sodium channel can be used both for the protection of the organs in the donor before and during removal, for the protection of removed organs, for example, also during storage thereof in physiological bath fluids, and also during transfer to the recipient's body. The combinations of an NCBE inhibitor with a blocker of the non-inactivating sodium channel are likewise valuable, protectively acting pharmaceuticals when carrying out angioplastic surgical interventions, for example on the heart, and also on peripheral vessels. In accordance with their protective action against ischemically induced damage, the combinations of an NCBE inhibitor with a blocker of the non-inactivating sodium channel are also suitable as pharmaceuticals for the treatment of ischemias of the nervous system, in particular of the central nervous system, where they are suitable for the treatment of stroke or of cerebral edema. Moreover, the combinations according to the invention of an NCBE inhibitor with a blocker of the non-inactivating sodium channel are also suitable for the treatment of forms of shock, such as, for example, of allergic, cardiogenic, hypovolemic and bacterial shock.

Beside administration as a fixed combination, the invention also relates to the simultaneous, separate or sequential administration of NCBE inhibitors with NHE inhibitors and/or an additional active substance from another class of cardiovascular active compound for the treatment of the abovementioned diseases.

The invention additionally relates to a pharmaceutical preparation comprising a) an NCBE inhibitor and an NHE inhibitor and/or their physiologically tolerable salts; or b) an NCBE inhibitor and additionally an active substance from another class of cardiovascular active compound and/or their physiologically tolerable salts; or c) an NCBE inhibitor, an NHE inhibitor and additionally an active substance from another class of cardiovascular active compound, and/or their physiologically tolerable salts.

Preferred pharmaceutical preparations are those which contain a compound of the formula I and/or its physiologically tolerable salt as an NCBE inhibitor.

By combined administration, the effect of one combination component can be potentiated by the respective other component, i.e. the action and/or duration of action of a combination or preparation according to the invention is stronger or longer-lasting than the action and/or the duration of action of the respective individual components (synergistic effect). In the case of combined administration, this leads to a lowering of the dose of the respective combination component, compared with individual administration. The combinations and preparations according to the invention accordingly have the advantage that the amounts of active compound to be administered can be significantly reduced and undesirable side effects can be eliminated or greatly reduced.

The invention furthermore relates to a commercial pack, comprising as pharmaceutical active compound a) an NCBE inhibitor and an NHE inhibitor and/or their physiologically tolerable salts; or b) an NCBE inhibitor and additionally an active substance from another class of cardiovascular active compound and/or their physiologically tolerable salts; or c) an NCBE inhibitor, an NHE inhibitor and additionally an active substance from another class of cardiovascular active compound and/or their physiologically tolerable salts, in each case together with instructions for the use of these active compounds in combination for simultaneous, separate or sequential administration in the treatment or prophylaxis of the abovementioned syndromes, in particular for the treatment of cardiovascular disorders.

Preferred commercial packs are those which contain compounds of the formula I as NCBE inhibitors.

The pharmaceutical preparations according to the invention can be prepared, for example, by either intensively mixing the individual components as powders, or by dissolving the individual components in the suitable solvents such as, for example, a lower alcohol and then removing the solvent.

The weight ratio of NCBE inhibitor to the NHE inhibitor or the substance having cardiovascular activity in the combinations and preparations according to the invention is expediently 1:0.01 to 1:100, preferably 1:0.1 to 1:10.

The combination and preparations according to the invention contain a total of preferably 0.5–99.5% by weight, in particular 4–99% by weight, of these active compounds.

When used according to the invention in mammals, preferably in man, the doses of the various active compound components vary, for example, in the range from 0.001 to 100 mg/kg/day.

List of Abbreviations

| | |
|---|---|
| Bn | Benzyl |
| $CH_2Cl_2$ | Dichloromethane |
| DCI | Desorption-chemical ionization |
| DIP | Diisopropyl ether |
| DMA | Dimethylacetamide |
| DME | Dimethoxyethane |
| DMF | N,N-Dimethylformamide |
| EA | Ethyl acetate (EtOAc) |
| EI | Electron impact |
| eq | Equivalent |
| ES | Electrospray ionization |
| Et | Ethyl |
| FAB | Fast atom bombardment |
| HEP | n-Heptane |
| HOAc | Acetic acid |
| Me | Methyl |
| MeOH | Methanol |
| mp | Melting point |
| MTB | methyl tertiary-butyl ether |
| NCBE | sodium-dependent chloride/bicarbonate exchanger |
| NHE | Sodium/hydrogen exchanger |
| NMP | N-Methylpyrrolidone |
| RT | Room temperature |
| THF | Tetrahydrofuran |
| TMU | N,N,N',N'-Tetramethylurea |
| Tol | Toluene |
| CNS | Central nervous system |

General Procedure for the Preparation of Sulfonylcyanamides from Sulfonamides

The sulfonamide starting material is dissolved in 10 ml/mmol of anhydrous acetonitrile, 3 mol equivalents of $K_2CO_3$ and one mol equivalent of a 5 N solution of BrCN in acetonitrile are added dropwise and the mixture is heated under reflux until conversion is complete (typical reaction time 1–6 hours). The reaction mixture is then chromatographed on silica gel without further working up.

EXAMPLE 1

Ethyl 2-Butyl-5-methylsulfanyl-3-(2'-cyanoaminosulfonyl-biphenyl-4-ylmethyl)-3H-imidazole-4-carboxylate

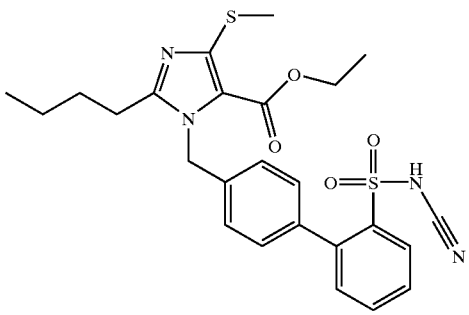

975 mg of ethyl 1-[[2'-(aminosulfonyl)(1,1'-biphenyl)-4-yl]methyl]-2-butyl-4-(methylthio)-1H-imidazole-5-carboxylate (J. Med. Chem. 1995, 38, 2357) were dissolved in 10 ml of anhydrous acetonitrile, then 276 mg of $K_2CO_3$ and 2 ml of a 1 N cyanogen bromide solution in acetonitrile were added, and the mixture was heated under reflux for 4 h. The reaction mixture was chromatographed on silica gel using EA/MeOH 10:1, and after allowing to crystallize, 780 mg of a colorless amorphous solid were obtained with decomposition.

mp 111° C. with decomposition, $R_f$ (EA/MeOH 10:1)= 0.20 MS (FAB): 513 (M+H)$^+$.

EXAMPLE 2

Ethyl 2-Butyl-5-methylsulfanyl-3-(3'-cyanoaminosulfonyl-biphenyl-4-ylmethyl)-3H-imidazole-4-carboxylate

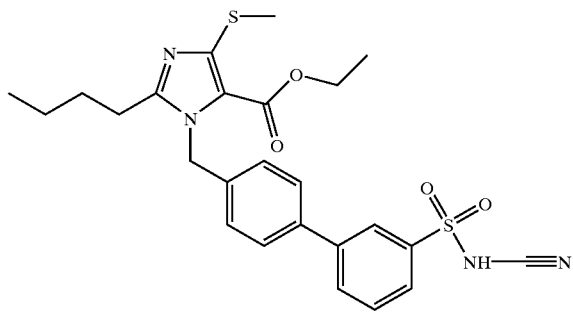

a) 3-Bromo-N-dimethylaminomethylenebenzenesulfonamide 20.3 g of 3-bromobenzenesulfonamide were dissolved in 120 ml of DMF and 57 ml of dimethylformamide dimethyl acetal were added dropwise at RT. The mixture was stirred at RT for 5 h and allowed to stand at RT for 3 days. The reaction mixture was then poured onto 1.2 l of water and stirred for 90 minutes, and the white precipitate was filtered off. The product was dried at 50° C. in vacuo, and 20.5 g of white crystals were obtained, mp 122° C. $R_f$ (EA)=0.59 MS (DCI): 291 (M+H)⁺.

b) 4'-Methylbiphenyl-3-sulfonic Acid Dimethylaminomethylenamide 2.9 g of 3-bromo-N-dimethylaminomethylenebenzenesulfonamide, 1.5 g of p-tolylboronic acid, 112 mg of Pd(II) acetate and 224 mg of triphenylphosphine were dissolved in 60 ml of toluene and 17 ml of ethanol, 10 ml of a 2 N aqueous $Na_2CO_3$ solution were added and the mixture was refluxed for 7 h. The reaction mixture was taken up in 150 ml of a saturated aqueous $Na_2CO_3$ solution and 150 ml of water and extracted 3 times with 200 ml of EA each time. The extract was dried over $Na_2SO_4$ and the solvent was removed in vacuo. Chromatography on silica gel using MTB yielded 1.8 g of a colorless foam.

$R_f$ (EA/HEP 2:1)=0.22 MS (DCI): 302 (M+H)⁺.

c) 4'-Bromomethylbiphenyl-3-sulfonic Acid Dimethylaminomethylenamide 1.7 g of 4'-methylbiphenyl-3-sulfonic acid dimethylaminomethylenamide were dissolved in 30 ml of chlorobenzene and 1.0 g of N-bromosuccin-imide and 10 mg of benzoyl peroxide were added at 130° C. and the mixture was refluxed for 30 minutes. The reaction mixture was taken up using 150 ml of EA and washed twice with 150 ml each time of an 8:1 mixture of saturated aqueous $Na_2CO_3$ solution and saturated aqueous $Na_2SO_3$ solution. The aqueous phase was then extracted a further 2 times with 150 ml of EA each time. The combined organic phase was dried over $Na_2SO_4$ and the solvent was removed in vacuo. Chromatography on silica gel using MTB yielded 1.6 g of a pale yellow oil.

$R_f$ (EA)=0.59 MS (DCI) 291 (M+H)⁺.

d) Ethyl 2-Butyl-3-[3'-(dimethylaminomethylenesulfamoyl)biphenyl-4-yl-methyl]-5-(methylsulfanyl)-3H-imidazole-4-carboxylate 1.6 g of 4'-bromomethylbiphenyl-3-sulfonic acid dimethylaminomethylen-amide, 990 mg of ethyl 2-butyl-5-methylsulfanyl-3H-imidazole-4-carboxylate (J. Med. Chem. 1995, 38, 2357) and 570 mg of $K_2CO_3$ were stirred for 4 h at RT in 12 ml of DMF and allowed to stand overnight. The reaction mixture was then stirred at RT for a further 6 h, then poured into 125 ml of a saturated aqueous $NaHCO_3$ solution and 125 ml of water and extract 3 times using 200 ml of EA each time. The extracted was dried over $Na_2SO_4$ and the solvent was removed in vacuo. Chromatography on silica gel using EA/HEP 2:1 yielded 1.1 g of a colorless oil.

$R_f$ (EA/HEP 1:1)=0.10 MS (ES):543 (M+H)⁺.

e) Ethyl 2-Butyl-5-methylsulfanyl-3-(3'-sulfamoylbiphenyl-4-ylmethyl)-3H-imidazole-4-carboxylate 1.1 g of ethyl 2-butyl-3-[3'-(dimethylaminomethylenesulfamoyl)biphenyl-4-ylmethyl]-5-(methylsulfanyl)-3H-imidazole-4-carboxylate were dissolved in 20 ml of methanol and 10 ml of a saturated aqueous HCl solution were added. The mixture was heated under reflux for 4 h, then adjusted to pH=5–6 using an aqueous 6 N NaOH solution, diluted with 50 ml of water and extracted 3 times using 150 ml of EA each time. The extract was dried over $Na_2SO_4$ and the solvent was removed in vacuo. Chromatography on silica gel using EA/HEP 1:1 yielded 950 mg of a colorless foam.

$R_f$ (EA/HEP 1:1)=0.38 MS (ES) 488 (M+H)⁺.

f) Ethyl 2-Butyl-5-methylsulfanyl-3-(3'-cyanoaminosulfonylbiphenyl-4-ylmethyl)-3H-imidazole-4-carboxylate 720 mg of ethyl 2-butyl-5-methylsulfanyl-3-(3'-sulfamoylbiphenyl-4-yl-methyl)-3H-imidazole-4-carboxylate were reacted according to the general procedure for the preparation of sulfonylcyanamides from sulfonamides, and 550 mg of an amorphous solid were obtained.

$R_f$ (EA/MeOH 10:1)=0.38 MS (ES): 513 (M+H)⁺.

The title compounds of Examples 3–9 were synthesized analogously to Example 2:

EXAMPLE 3

Ethyl 2-Butyl-5-methylsulfanyl-3-(4'-cyanoaminosulfonyl-biphenyl-4-ylmethyl)-3H-imidazole-4-carboxylate

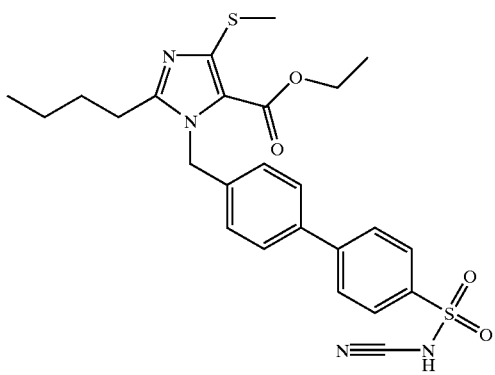

mp 244° C. with decomposition $R_f$ (EA/MeOH 10:1)=0.17 MS (ES): 513 (M+H)⁺.

EXAMPLE 4

Ethyl 2-Butyl-5-methylsulfanyl-3-(2'-cyanoaminosulfonyl-biphenyl-3-ylmethyl)-3H-imidazole-4-carboxylate

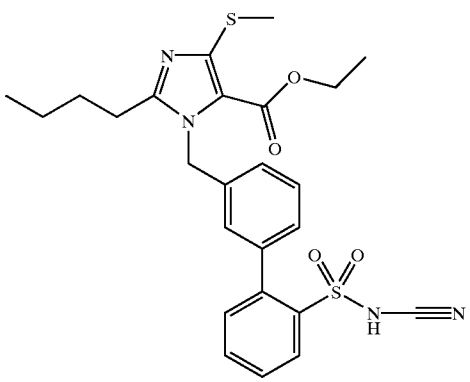

mp 118° C. with decomposition $R_f$ (E=MeOH 10:1) 0.19 MS (ES): 513 (M+H)⁺.

EXAMPLE 5

Ethyl 2-Butyl-5-methylsulfanyl-3-(3'-cyanoaminosulfonyl-biphenyl-3-ylmethyl)-3H-imidazole-4-carboxylate

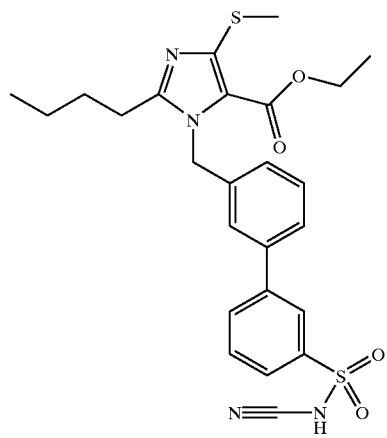

mp 112° C. with decomposition $R_f$ (EA/MeOH 10:1)= 0.15 MS (ES): 513 (M+H)$^+$.

EXAMPLE 6

Ethyl 2-Butyl-5-methylsulfanyl-3-(4'-cyanoaminosulfonyl-biphenyl-3-ylmethyl)-3H-imidazole-4-carboxylate

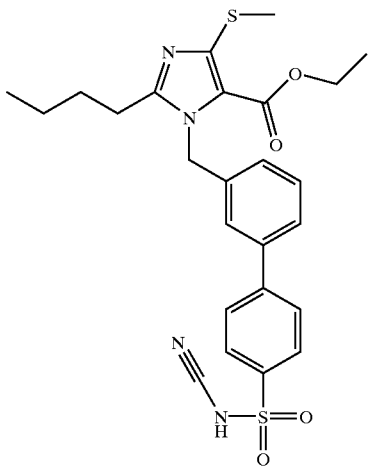

mp 120° C. with decomposition $R_f$ (EA/MeOH 10:1)= 0.36 MS (ES):513 (M+H)$^+$.

EXAMPLE 7

Ethyl 2-Butyl-5-methylsulfanyl-3-(2'-cyanoaminosulfonyl-biphenyl-2-ylmethyl)-3H-imidazole-4-carboxylate

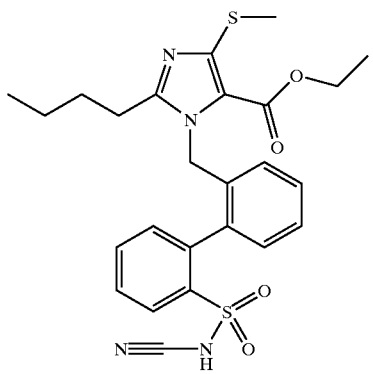

mp 105° C. with decomposition $R_f$ (EA/MeOH 10:1): 0.23 MS (ES): 513 (M+H)$^+$.

EXAMPLE 8

Ethyl 2-Butyl-5-methylsulfanyl-3-(3'cyanoaminosulfonyl-biphenyl-2-ylmethyl)-3H-imidazole-4-carboxylate

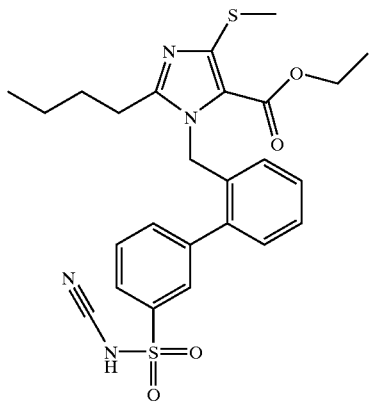

mp 108° C. with decomposition $R_f$ (EA/MeOH 10:1)= 0.27 MS (ES): 513 (M+H)$^+$.

EXAMPLE 9

Ethyl 2-Butyl-5-methylsulfanyl-3-(4'-cyanoaminosulfonyl-biphenyl-2-ylmethyl)-3H-imidazole-4-carboxylate

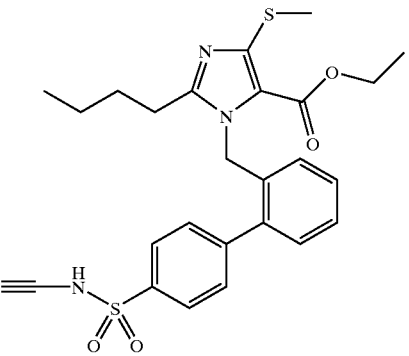

mp 116° C. with decomposition $R_f$ (EA/MeOH 10:1)= 0.23 MS (ES): 513 (M+H)$^+$.

The title compound of Example 10 was synthesized from ethyl 2-cyclo-propyl-5-methylsulfanyl-3-(4'-sulfamoylbiphenyl-2-ylmethyl)-3H-imidazole-4-carboxylate (J. Med. Chem. 1995, 38, 2357) analogously to Example 2:

EXAMPLE 10

Ethyl 2-Cyclopropyl-5-methylsulfanyl-3-(2'-cyanoaminosulfonyl-biphenyl-4-ylmethyl)-3H-imidazole-4-carboxylate

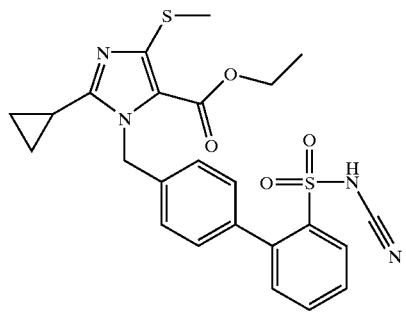

mp >260° C. $R_f$ (EA/MeOH 10:1)=0.30 MS (ES): :497 (M+H)$^+$.

EXAMPLE 11

4'-(4-Chloro-5-formyl-2-phenylimidazol-1-ylmethyl)biphenyl-2-sulfonylcyanamide

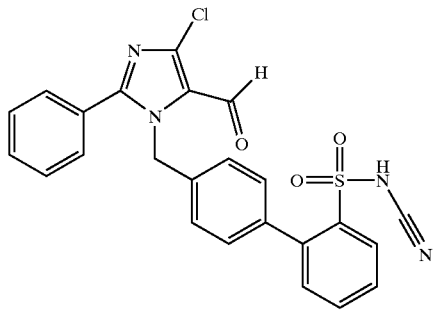

a) 4'-(4-Chloro-5-formyl-2-phenylimidazol-1-ylmethyl)biphenyl-2-sulfonic Acid Dimethylaminomethylenamide 2.1 g of 4-chloro-5-formyl-2-phenylimidazole (Chem. Pharm. Bull. 1976, 24(5), 960), 3.8 g of 4'-bromomethylbiphenyl-2-sulfonic acid dimethylaminomethylenamide (J. Med. Chem. 1995, 38, 2357) and 2.8 g of $K_2CO_3$ were stirred at RT for 30 h in 50 ml of DMF. The reaction mixture was poured onto 500 ml of water and extracted 2 times using 250 ml of EA each time. The organic phase was then washed with 100 ml of water and dried over $MgSO_4$, and the solvent was removed in vacuo. Chromatography on silica gel using MTB yielded 1.9 g of a white, crystalline powder, mp 193° C.

$R_f$ (MTB)=0.19 MS (ES): 507 (M+H)$^+$.

b) 4'-(4-Chloro-5-formyl-2-phenylimidazol-1-ylmethyl)biphenyl-2-sulfonamide 1.9 g of 4'-(4-chloro-5-formyl-2-phenylimidazol-1-ylmethyl)biphenyl-2-sulfonic acid dimethylaminomethylenamide were dissolved in 20 ml of ethanol and 20 ml of a saturated aqueous HCl solution were added. The mixture was heated under reflux for 2 hours, then the volatile constituents were removed in vacuo, the residue was taken up using 200 ml of water, the solution was adjusted to pH–7 using aqueous NaOH solution and stirred for 1 hour, and the precipitate was filtered off with suction. The product was dried in vacuo, and 1.7 g of a colorless solid were obtained, mp 215° C. with decomposition. $R_f$ (MTB)=0.57 MS (FAB): 452 (M+H)$^+$.

c) 4'-(4-Chloro-5-formyl-2-phenylimidazol-1-ylmethyl)biphenyl-2-sulfonyl-cyanamide 800 mg of 4'-(4-chloro-5-formyl-2-phenylimidazol-1-ylmethyl)biphenyl-2-sulfonamide were reacted according to the general procedure for the preparation of sulfonylcyanamides from sulfonamides, and 650 mg of an amorphous solid were obtained.

$R_f$ (EA/MeOH 10:1)=0.18 MS (ES): 477 (M+H)$^+$.

EXAMPLE 12

4'-(4-Methoxy-5-formyl-2-phenylimidazol-1-ylmethyl)biphenyl-2-sulfonylcyanamide

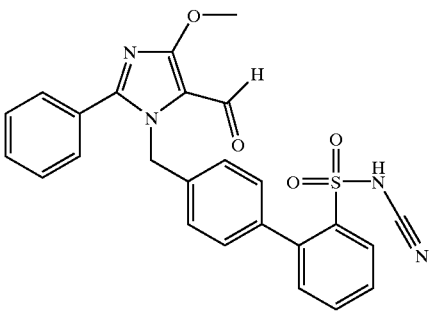

a) 4'-(4-Methoxy-5-formyl-2-phenylimidazol-1-ylmethyl)biphenyl-2-sulfon-amide 700 mg of 4'-(4-chloro-5-formyl-2-phenylimidazol-1-ylmethyl)biphenyl-2-sulfonamide (Example 11 b) and 620 mg of NaOH were dissolved in 10 ml of methanol and heated under reflux for 1 hour. The solvent was removed in vacuo, the residue was taken up with 20 ml of water, the solution was adjusted to pH=7 using aqueous HCl solution and the precipitate was filtered off. It was dried in vacuo, and 650 mg of a colorless solid were obtained, mp 188° C. $R_f$ (DIP/MTB 1:1)=0.26 MS (FAB):448 (M+H)$^+$.

b) 4'-(4-Methoxy-5-formyl-2-phenylimidazol-1-ylmethyl)biphenyl-2-sulfonyl-cyanamide 650 mg of 4'-(4-methoxy-5-formyl-2-phenylimidazol-1-ylmethyl)biphenyl-2-sulfonamide were reacted according to the general procedure for the preparation of sulfonylcyanamides from sulfonamides, and 600 mg of an amorphous solid were obtained.

$R_f$ (EA/MeOH 10:1)=0.18 MS (ES): 472 (M+H)$^+$.

EXAMPLE 13

Ethyl 2-Butyl-3-(2'-cyanoaminosulfonylbiphenyl-4-ylmethyl)-3H-imidazole-4-carboxylate

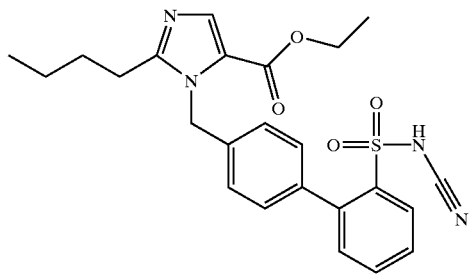

a) Ethyl 1-[[2'-(Aminosulfonyl)(1,1'-biphenyl)-4-yl]methyl]-2-butyl-1-H-imid-azole-5-carboxylate 244 mg of ethyl 1-[[2'-(aminosulfonyl)(1,1'-biphenyl)-4-yl]methyl]-2-butyl-4-(methylthio)-1-H-imidazole-5-carboxylate (J. Med. Chem. 1995, 38, 2357) are dissolved in 10 ml of ethanol and 200 mg of Raney nickel are added. The mixture is then refluxed for 6 h, a further 200 mg of Raney nickel are added and it is again refluxed for 3 h. The residue is filtered off and the solvent is removed in vacuo. 200 mg of a colorless oil are obtained.

$R_f$ (MTB/DIP 1:1)=0.12 MS (FAB): 442 (M+H)$^+$.

b) Ethyl 2-Butyl-3-(2'-cyanoaminosulfonylbiphenyl-4-ylmethyl)-3H-imidazole-4-carboxylate 140 mg of ethyl 1-[[2'-(aminosulfonyl)(1, 1'-biphenyl)-4-yl]methyl]-2-butyl-1H-imidazole-5-carboxylate are reacted according to the general procedure for the preparation of sulfonylcyanamides from sulfonamides (reaction time 1 h) and 90 mg of white crystals are obtained, mp 121° C. with decomposition.

$R_f$ (EA/MeOH 5:1)=0.20 IR (C≡N):2174.7 cm$^{-1}$ MS (ES): 467 (M+H)$^+$.

EXAMPLE 14

4'-(2-Butyl-5-cyano-4-methoxyimidazol-1-ylmethyl)biphenyl-2-sulfonylcyanamide

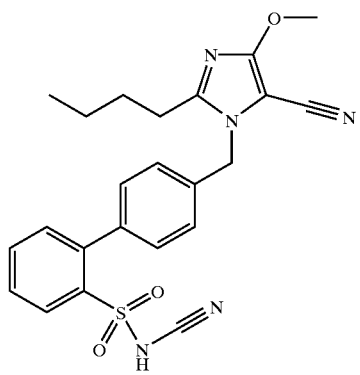

a) 4'-[2-Butyl-5-(hydroxyiminomethyl)-4-methoxyimidazol-1-ylmethyl]-biphenyl-2-sulfonamide 4.1 g of 4'-(4-methoxy-5-formyl-2-phenylimidazol-1-ylmethyl)biphenyl-2-sulfonamide (Example 12a) are dissolved in 500 ml of methanol and 3.3 g of hydroxylamine hydrochloride and 1.2 g of 1,4-diazabicyclo[2.2.2]octane are added. The mixture is stirred at RT for 11 h, then treated with 200 ml of a saturated aqueous NaHCO$_3$ solution and 200 ml of water and extracted 6 times using 400 ml of EA each time. The extract is dried over Na$_2$SO$_4$ and the solvents are removed in vacuo. 4.5 g of a colorless oil are obtained.

$R_f$ (MTB/toluene 1:1)=0.32 b) 4'-(2-Butyl-5-cyano-4-methoxyimidazol-1-ylmethyl)biphenyl-2-sulfonic Acid Acetylamide 210 mg of 4'-[2-butyl-5-(hydroxyiminomethyl)-4-methoxyimidazol-1-ylmethyl]-biphenyl-2-sulfonamide are dissolved in 4 ml of pyridine and 4 ml of acetic anhydride are added. The mixture is refluxed for 170 minutes, then poured onto 200 ml of an ice-cooled, saturated aqueous NaHCO$_3$ solution and extracted 3 times using 80 ml of EA each time. The extract is dried over Na$_2$SO$_4$ and the solvent is removed in vacuo. 230 mg of a colorless oil are obtained.

$R_f$ (MTB/toluene 1:1)=0.14 MS (FAB): 467 (M+H)$^+$.

c) 4'-(2-Butyl-5-.cyano-4-methoxyimidazol-1-ylmethyl)biphenyl-2-sulfonamide 2.1 g of 4'-(2-butyl-5-cyano-4-methoxyimidazol-1-ylmethyl)biphenyl-2-sulfonic acid acetylamide are suspended in 40 ml of a 20% aqueous H$_2$SO$_4$ solution and the mixture is refluxed for 3 h. The reaction mixture is added dropwise to 400 ml of a 2/3 M solution of KH$_2$PO$_4$ in water and extracted 3 times using 300 ml of EA each time. The extract is dried over Na$_2$SO$_4$ and the solvent is removed in vacuo. Chromatography on silica gel using MTB yields 1.6 g of a colorless oil.

$R_f$ (MTB)=0.48 d) 4'-(2-Butyl-5-cyano-4-methoxyimidazol-1-ylmethyl)biphenyl-2-sulfonyl-cyanamide 360 mg of 4'-(2-butyl-5-cyano-4-methoxyimidazol-1-ylmethyl)biphenyl-2-sulfonamide are reacted according to the general procedure for the preparation of sulfonylcyanamides from sulfonamides (reaction time 1 h) and 300 mg of white crystals are obtained, mp 160° C. with decomposition.

$R_f$ (EA/MeOH 5:1)=0.27 IR (C≡N): 2177.2 cm$^{-1}$ MS (ES): 450 (M+H)$^+$.

EXAMPLE 15

4'-(2-Butyl-4-chloro-5-formylimidazol-1-ylmethyl)biphenyl-2-sulfonylcyanamide

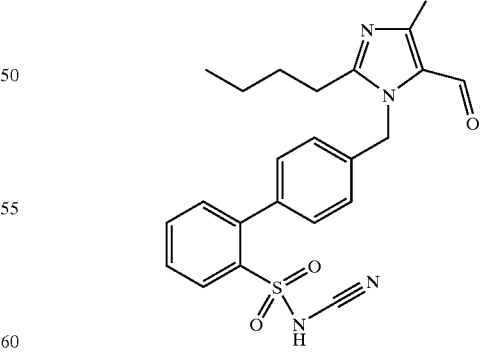

a) 4'-(2-Butyl-4-chloro-5-formylimidazol-1-ylmethyl)biphenyl-2-sulfonamide 10.6 g of 4'-(2-butyl-4-chloro-5-formylimidazol-1-ylmethyl)biphenyl-2-sulfonic acid dimethylaminomethyl-enamide (J. Med. Chem. 1995, 38, 2357) are dissolved in 200 ml of methanol and 100 ml of a saturated aqueous HCl solution are added. The mixture is refluxed for 2 h, adjusted to pH=5–6 with 2 N aqueous NaOH solution after cooling and extracted 4 times using 200 ml of EA each time. The extract is dried over $Na_2SO_4$ and the solvent is removed in vacuo. 9.2 g of a colorless oil are obtained.

$R_f$ (EA/HEP 2:1)=0.46 b) 4'-(2-Butyl-4-chloro-5-formylimidazol-1-ylmethyl) biphenyl-2-sulfonyl-cyanamide 160 mg of 4'-(2-butyl-4-chloro-5-formylimidazol-1-ylmethyl)biphenyl-2-sulfonamide are reacted according to the general procedure for the preparation of sulfonylcyanamides from sulfonamides (reaction time 75 minutes) and 110 mg of white crystals are obtained, mp 135° C. with decomposition.

$R_f$ (EA/MeOH 5:1)=0.28 IR (C≡N): 2176.9 cm$^{-1}$ MS (ESI): 457 (M+H)$^+$.

The title compounds of Examples 16–19 are synthesized analogously to Example 1:

EXAMPLE 16

Ethyl 5-Methylsulfanyl-2-propyl-3-(2'-sulfamoylbiphenyl-4-yl-methyl)-3H-imidazole-4-carboxylate

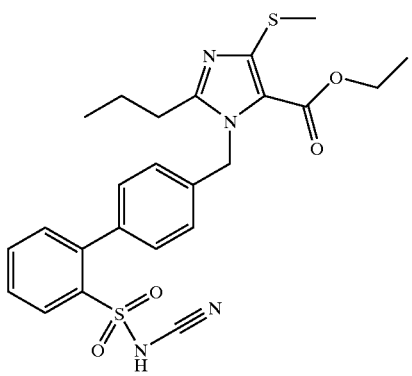

mp 165° C. (decomposition) $R_f$ (EA/MeOH 5:1)=0.42 IR (C≡N): 2178.6 cm$^{-1}$ MS (ES): 499 (M+H)$^+$.

EXAMPLE 17

Ethyl 2-Ethyl-5-methylsulfanyl-3-(2'-cyanoaminosulfonyl-biphenyl-4-ylmethyl)-3H-imidazole-4-carboxylate

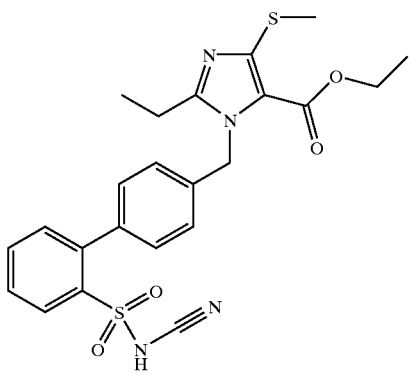

mp 94° C. (decomposition) $R_f$ (EA/MeOH 5:1)=0.38 IR (C≡N): 2173.3 cm$^{-1}$ MS (ES): 485 (M+H)$^+$.

EXAMPLE 18

Ethyl 2-Methyl-5-methylsulfanyl-3-(2'-cyanoaminosulfonyl-biphenyl-4-ylmethyl)-3H-imidazole-4-carboxylate

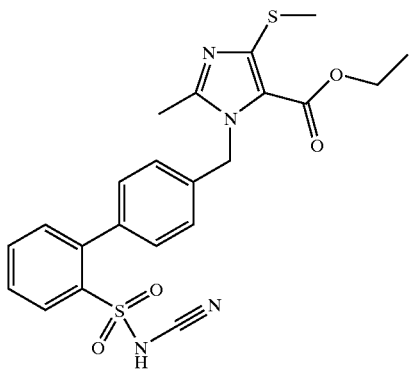

mp 169° C. (decomposition) $R_f$ (EA/MeOH 5:1)=0.29 IR (C≡N): 2173.0 cm$^{-1}$ MS (ES): 471 (M+H)$^+$.

EXAMPLE 19

Ethyl 2-Isopropyl-5-methylsulfanyl-3-(2'-cyanoaminosulfonyl-biphenyl-4-ylmethyl)-3H-imidazole-4-carboxylate

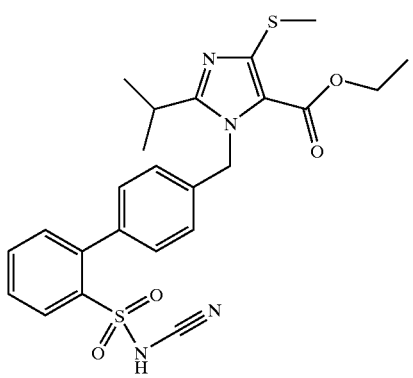

mp 276° C. (decomposition) $R_f$ (EA/MeOH 5:1)=0.28 IR (C≡N): 2178.8 cm$^{-1}$ MS (ES): 499 (M+H)$^+$.

EXAMPLE 20

Isopropyl 2-Butyl-5-methylsulfanyl-3-(2'-cyanoaminosulfonyl-biphenyl-4-ylmethyl)-3H-imidazole-4-carboxylate

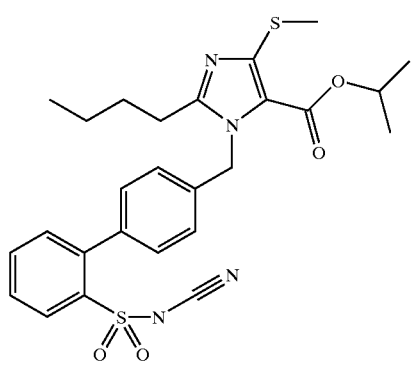

a) Isopropyl 2-Butyl-5-methylsulfanyl-3-(2'-sulfamoylbiphenyl-4-ylmethyl)-3H-imidazole-4-carboxylate 980 mg of ethyl 2-butyl-5-methylsulfanyl-3-(2'-sulfamoylbiphenyl-4-ylmethyl)-3H-imidazole-4-carboxylate are dissolved in ml of isopropanol and 590 µl of titanium(IV) isopropoxide are added. The mixture is refluxed for 9 h and a further 590 µl of titanium(IV) isopropoxide are then added. The mixture is refluxed for 8 h and 1.2 ml of titanium(IV) isopropoxide are again added. After reflux for a further 11 h, the mixture is poured onto 200 ml of a saturated aqueous $NaHCO_3$ solution and diluted with 200 ml of water. It is extracted 3 times using 150 ml of EA each time, the extract is dried over $Na_2SO_4$ and the solvent is removed in vacuo. Chromatography on silica gel using EA/HEP 1:2 yields 420 mg of a colorless oil.

$R_f$ (MTB/HEP/$CHCl_3$ 2:1:1)=0.36 b) Isopropyl 2-Butyl-5-methylsulfanyl-3-(2'-cyanoaminosulfonylbiphenyl-4-yl-methyl)-3H-imidazole-4-carboxylate 410 mg of isopropyl 2-butyl-5-methylsulfanyl-3-(2'-sulfamoylbiphenyl-4-ylmethyl)-3H-imidazole-4-carboxylate are reacted according to the general procedure for the preparation of sulfonylcyanamides from sulfonamides (reaction time 2 h) and 310 mg of white crystals are obtained, mp 113° C. with decomposition.

$R_f$ (EA/MeOH 5:1)=0.16 IR (C≡N): 2178.2 $cm^{-1}$ MS (ES): 527 $(M+H)^+$.

EXAMPLE 21

Ethyl 2-Butyl-3-(2'-methyl-5'-cyanoaminosulfonylbiphenyl-4yl-methyl)-5-methylsulfanyl-3H-imidazole-4-carboxylate

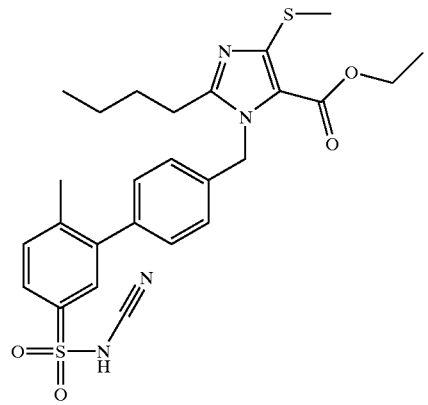

a) 4,4,5,5-Tetramethyl-2-p-tolyl[1.3.2]dioxaborolane 1.4 g of p-tolylboronic acid, 1.2 g of pinacol and a catalytic amount (approximately 2 mg) of p-toluenesulfonic acid are suspended 3 times in 40 ml of toluene each time and the volatile constituents are in each case removed in vacuo. The mixture is then dried in a fine vacuum and 2.0 g of a pale yellow oil are obtained.

$R_f$ (EA/HEP 1:1)=0.86 b) 2-(4-Bromomethylphenyl)-4,4,5,5-tetramethyl[1.3.2]dioxaborolane 2.0 g of 4,4,5,5-tetramethyl-2-p-tolyl[1.3.2]dioxaborolane are dissolved in 50 ml of chlorobenzene and 1.7 g of N-bromosuccinimide and 5 mg of benzoyl peroxide are added in portions at boiling temperature. The mixture is refluxed for 4 h and diluted with 200 ml of EA after cooling. It is washed twice with 100 ml each time of an 8:1 mixture of saturated aqueous $NaHCO_3$ solution and saturated aqueous $Na_2SO_4$ solution, then the aqueous phase is extracted a further 2 times with 100 ml of EA each time and the combined organic phases are dried over $Na_2SO_4$. The solvents are removed in vacuo and chromatography on silica gel using EA/HEP 1:4 yields 1.6 g of a pale yellow oil.

$R_f$ (EA/HEP 1:4)=0.55 MS (DCI): 297 $(M+H)^+$.

c) Ethyl 2-Butyl-5-methylsulfanyl-3-[4-(4,4,5,5-tetramethyl[1.3.2]dioxa-borolan-2-yl)benzyl]-3H-imidazole-4-carboxylate 1.5 g of 2-(4-bromomethylphenyl)-4,4,5,5-tetramethyl[1.3.2]dioxaborolane, 1.2 g of ethyl 2-butyl-5-methylsulfanyl-3H-imidazole-4-carboxylate (J. Med. Chem. 1995, 38, 2357) and 700 mg of $K_2CO_3$ are stirred at RT for 14 h in 15 ml of DMF. The reaction mixture is poured onto 200 ml of a saturated aqueous $NaHCO_3$ solution, diluted with 200 ml of water and extracted 3 times using 150 ml of EA each time. The extract is dried over $Na_2SO_4$ and the solvent is removed in vacuo. Chromatography on silica gel using EA/HEP 1:4 yields 1.4 g of a colorless oil.

$R_f$ (EA/HEP 1:2)=0.29 MS (FAB): 459 $(M+H)^+$.

d) Ethyl 2-butyl-5-methylsulfanyl-3-[4-(dihydroxyboryl)benzyl]-3H-imidazole-4-carboxylate 1.2 g of ethyl 2-butyl-5-methylsulfanyl-3-[4-(4,4,5,5-tetramethyl[1.3.2]dioxa-borolan-2-yl)benzyl]-3H-imidazole-4-carboxylate are dissolved in 50 ml of EA and 260 µl of diethanolamine are added. The mixture is stirred at RT for 5 h, then treated at RT for 4 h in an ultrasonic cleaning bath. 260 µl of diethanolamine are then added and the mixture is treated for a further 2 h in the ultrasonic cleaning bath. It is then stirred at RT for 14 h and the precipitate is filtered off. This precipitate is taken up in 50 ml of a half-concentrated aqueous NaHSO$_4$ solution and this is stirred at RT for 2 h. It is then extracted 3 times with 150 ml of EA each time, the extract is dried over Na$_2$SO$_4$ and the solvent is removed in vacuo. 390 mg of an amorphous solid are obtained.

R$_f$ (EA) 0.62 MS (FAB, +glycerol): 433 (M+56+H)$^+$.

e) 3-Bromo-4-methylbenzenesulfonamide 10 g of 3-bromo-4-methylaniline are suspended in 22 ml of water and 22 ml of a saturated aqueous HCl solution are added dropwise. The mixture is stirred at RT for 5 minutes and then brought to −10° C., and a solution of 4.1 g of NaNO$_2$ in 15 ml of water is added dropwise at this temperature. The mixture is stirred at −15° C. for 45 minutes and added in portions to a suspension of 916 mg of CuCl$_2$×2 H$_2$O and 92 mg of CuCl in a saturated solution of SO$_2$ in glacial acetic acid at RT. The reaction mixture is slowly warmed on the water bath until the evolution of nitrogen is complete. It is then extracted 3 times with 250 ml of diethyl ether each time, and the organic phase is washed twice with 80 ml of water each time and dried over Na$_2$SO$_4$. The solvent is removed in vacuo, the residue is taken up using 75 ml of acetone, the solution is cooled to 0° C. and a saturated aqueous NH$_3$ solution is slowly added dropwise at this temperature until the pH reaches 10. During the course of this a precipitate deposits, which is filtered off and recrystallized from MTB. 2.5 g of white crystals are obtained, mp 156° C.

R$_f$ (DIP)=0.30 MS (DCI): 250 (M+H)$^+$.

f) 3-Bromo-N-dimethylaminomethylene-4-methylbenzenesulfonamide 7.7 g of 3-bromo-4-methylbenzenesulfonamide are dissolved in 50 ml of DMF and 20.5 ml of dimethylformamide dimethyl acetal are added dropwise at RT. The mixture is stirred at RT for 4½ h and the product is then filtered off with suction and dried in vacuo. 9.0 g of pale yellow crystals are obtained, mp 162° C.

R$_f$ (EA)=0.48 MS (ES): 305 (M+H)$^+$.

g) Ethyl 2-butyl-3-[5'-(dimethylaminomethylenesulfamoyl)-2'-methylbiphenyl-4-ylmethyl]-5-methylsulfanyl-3H-imidazole-4-carboxylate 390 mg ethyl 2-butyl-5-methylsulfanyl-3-[4-(dihydroxyboryl)benzyl]-3H-imidazole-4-carboxylate, 288 mg of 3-bromo-N-dimethylaminomethylene-4-methylbenzenesulfonamide, 11 mg of Pd(II) acetate and 28 mg of triphenylphosphine are suspended in 6 ml of toluene and 1.6 ml of ethanol and 940 µl of a 2 M aqueous Na$_2$CO$_3$ solution are added. The reaction mixture is refluxed for 5¼ h, poured into 200 ml of a half-concentrated aqueous NaHCO$_3$ solution and extracted 3 times using 150 ml of EA each time. The extract is dried over Na$_2$SO$_4$ and the solvent is removed in vacuo. Chromatography on silica gel yields 150 mg of a colorless oil.

R$_f$ (EA/HEP 2:1)=0.19 MS (ES): 557 (M+H)$^+$.

h) Ethyl 2-Butyl-3-[5'-sulfamoyl-2'-methylbiphenyl-4-ylmethyl]-5-methyl-sulfanyl-3H-imidazole-4-carboxylate 140 mg of ethyl 2-butyl-3-[5'-(dimethylaminomethylenesulfamoyl)-2'-methyl-biphenyl-4-ylmethyl]-5-methylsulfanyl-3H-imidazole-4-carboxylate are dissolved in 2.5 ml of methanol and 1.3 ml of a saturated aqueous HCl solution are added dropwise. The reaction mixture is then refluxed for 75 minutes, adjusted to pH=6 with 6 N aqueous NaOH solution and diluted with 50 ml of water. It is extracted 5 times using 50 ml of EA each time, the extract is dried over Na$_2$SO$_4$ and the solvent is removed in vacuo. 110 mg of an amorphous solid are obtained.

R$_f$ (EA/HEP 2:1)=0.44 MS (ES): 502 (M+H)$^+$.

i) Ethyl 2-Butyl-3-(2'-methyl-5'-cyanoaminosulfonylbiphenyl-4-ylmethyl)-5-methylsulfanyl-3H-imidazole-4-carboxylate 100 mg of ethyl 2-butyl-3-[5'-sulfamoyl-2'-methylbiphenyl-4-ylmethyl]-5-methylsulfanyl-3H-imidazole-4-carboxylate are reacted according to the general procedure for the preparation of sulfonylcyanamides from sulfonamides (reaction time 1¾ h) and 63 mg of white crystals are obtained, mp 127° C. with decomposition.

R$_f$ (EA/MeOH 5:1)=0.09 IR (C≡N):2179.3 cm$^{-1}$ MS (ES): 527 (M+H)$^+$.

The title compounds of Examples 22–26 are synthesized analogously to Example 21:

EXAMPLE 22

Ethyl 2-Butyl-3-(2'-methyl-4'-cyanoaminosulfonylbiphenyl-4-yl-methyl)-5-methylsulfanyl-3H-imidazole-4-carboxylate

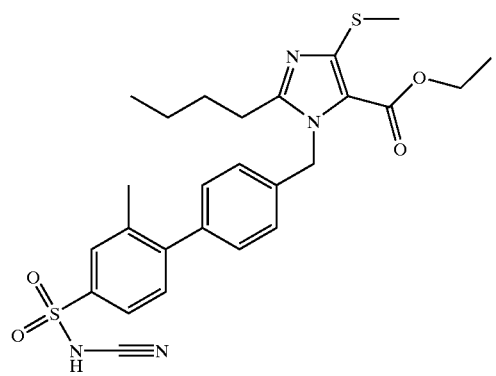

mp 211° C. R$_f$ (EA/MeOH 5:1)=0.20 IR (C≡N): 2182.9 cm$^{-1}$ MS (ES): 527 (M+H)$^+$.

EXAMPLE 23

Ethyl 2-Butyl-5-methylsulfanyl-3-(4'-cyanoaminosulfonyl-2'-trifluoromethylbiphenyl-4-ylmethyl)-3H-imidazole-4-carboxylate

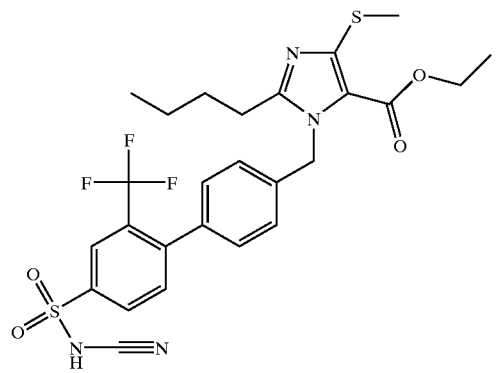

(amorphous) R$_f$ (EA/MeOH 10:1)=0.20 IR (C≡N): 2184.9 cm$^{-1}$ MS (ES): 581 (M+H)$^+$.

EXAMPLE 24

Ethyl 2-Butyl-3-(2'-methyl-5'-cyanoaminosulfonylbiphenyl-3-yl-methyl)-5-methylsulfanyl-3H-imidazole-4-carboxylate

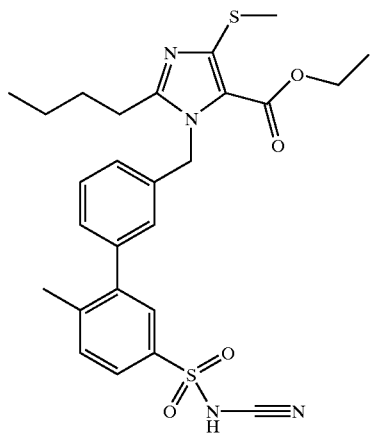

mp 160° C. (decomposition) $R_f$ (EA/MeOH 10:1)=0.18
IR (C≡N): 2181.3 cm$^{-1}$ MS (ES): 527 (M+H)$^+$.

EXAMPLE 25

Ethyl 2-Butyl-3-(2'-methyl-4'-cyanoaminosulfonylbiphenyl-3-yl-methyl)-5-methylsulfanyl-3H-imidazole-4-carboxylate

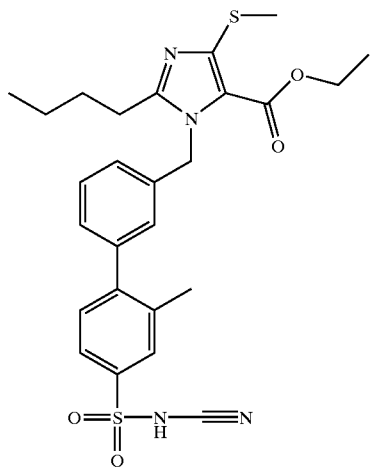

mp 115° C. (decomposition) $R_f$ (EA/MeOH 10:1)=0.18
IR (C≡N):2182.2 cm$^{-1}$ MS (ES): 527 (M+H)$^+$.

EXAMPLE 26

Ethyl 2-Butyl-5-methylsulfanyl-3-(4'-cyanoaminosulfonyl-2'-trifluoromethylbiphenyl-3-ylmethyl)-3H-imidazole-4-carboxylate

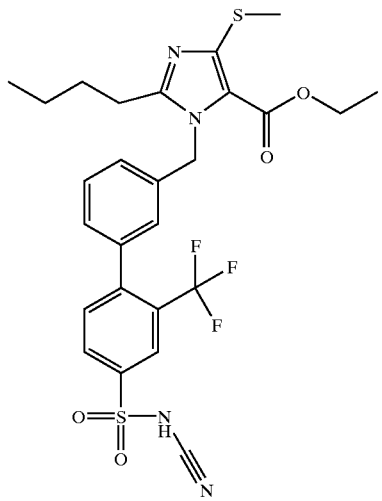

mp 122° C. (decomposition) $R_f$ (EA/MeOH 10:1)=0.27
IR (C≡N): 2186.1 cm$^{-1}$ MS (ES): 581 (M+H)$^+$.

EXAMPLE 27

4'-(2-Butyl-4-methylsulfanylimidazol-1-ylmethyl)biphenyl-2-sulfonylcyanamide

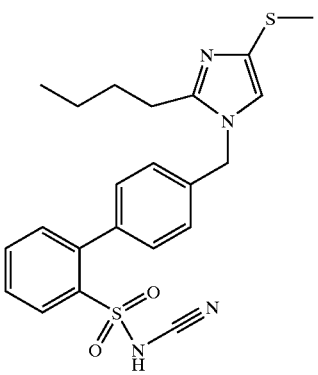

a) 4'-(2-Butyl-4-methylsulfanylimidazol-1-ylmethyl)biphenyl-2-sulfonamide 460 mg of 2-butyl-5-methylsulfanyl-3-(2'-sulfamoylbiphenyl-4-ylmethyl)-3H-imidazole-4-carboxylic acid are dissolved in 5 ml of isopropanol, 220 μl of thionyl chloride are added by syringe and the mixture is refluxed for 4¾ h. The mixture is then adjusted to pH=6 using a 6 N aqueous NaOH solution, diluted with 100 ml of water and extracted 3 times using 100 ml of EA each time. The extract is dried over Na$_2$SO$_4$ and the solvent is removed in vacuo. Chromatography on silica gel using EA/HEP 1:1 yields 300 mg of a colorless oil.

$R_f$ (EA)=0.58 MS (FAB): 416 (M+H)$^+$.

b) 4'-(2-Butyl-4-methylsulfanylimidazol-1-ylmethyl)biphenyl-2-sulfonyl-cyanamide 260 mg of 4'-(2-butyl-4-methylsulfanylimidazol-1-ylmethyl)biphenyl-2-sulfonamide are reacted according to the general procedure for the preparation of sulfonylcyanamides from sulfonamides (reaction time 2 h 20 minutes) and 50 mg of an amorphous powder are obtained.

$R_f$ (EA/MeOH 5:1)=0.19 IR (C≡N):2171.8 cm$^1$ MS (ES):441 (M+H)$^+$.

EXAMPLE 28

4'-(4-Chloro-2-phenylimidazol-1-ylmethyl)biphenyl-2-sulfonylcyanamide

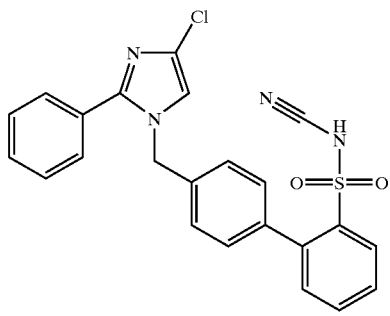

a) 4'-(4-Chloro-2-phenylimidazol-1-ylmethyl)biphenyl-2-sulfonamide 9.2 g of 4'-(4-chloro-5-formyl-2-phenylimidazol-1-ylmethyl)biphenyl-2-sulfonic acid dimethylaminomethylenamide (Example 11a), 95 ml of a saturated aqueous HCl solution and 95 ml of ethanol are refluxed for 2 h. After cooling, the mixture is diluted with 500 ml of water and extracted twice using 500 ml of EA each time and the organic phase is washed twice using 100 ml of a saturated aqueous NaCl solution each time. The extract is dried over Na$_2$SO$_4$ and the solvent is removed in vacuo. The product mixture is recrystallized from 200 ml of EA and 6.2 g of 4'-(4-chloro-5-formyl-2-phenyl-imidazol-1-ylmethyl) biphenyl-2-sulfonamide (compare Example 11b) are obtained. The solvent of the mother liquor is removed in vacuo and the residue is chromatographed on silica gel using MTB/DIP 1:1. 40 mg of a colorless oil are obtained.

$R_f$ (MTB/DIP 1:1)=0.22 MS (ES):424 (M+H)$^+$.

b) 4'-(4-Chloro-2-phenylimidazol-1-ylmethyl)biphenyl-2-sulfonylcyanamide 30 mg of 4'-(4-chloro-2-phenylimidazol-1-ylmethyl) biphenyl-2-sulfonamide are reacted according to the general procedure for the preparation of sulfonylcyanamides from sulfonamides (reaction time 2 h) and 15 mg of an amorphous powder are obtained.

$R_f$ (EA/MeOH 10:1)=0.09 MS (ES–): 447 (M–H)$^-$. ES–: electron spray, negative mode

EXAMPLE 29

4'-(5-Acetyl-4-chloro-2-phenylimidazol-1-ylmethyl) biphenyl-2-sulfonylcyanamide

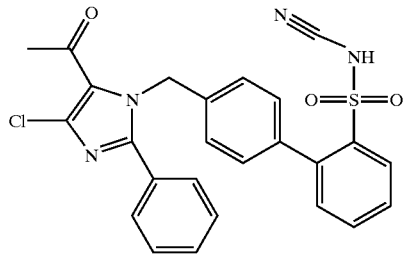

a) 3-(4-Bromobenzyl)-5-chloro-2-phenyl-3H-imidazole-4-carbaldehyde 3.0 g of 4-chloro-5-formyl-2-phenylimidazole (Chem. Pharm. Bull. 1976, 24(5), 960), 7.0 g of 4-bromobenzyl bromide and 11.7 g of K$_2$CO$_3$ are stirred at RT for 20 h in 200 ml of DMF. The reaction mixture is then poured onto 500 ml of water, and the precipitate is filtered off with suction and chromatographed on silica gel using DIP. 3.9 g of an amorphous foam are obtained.

$R_f$ (DIP)=0.36 MS (ES): 375 (M+H)$^+$.

b) 1-[3-(4-Bromobenzyl)-5-chloro-2-phenyl-3H-imidazol-4-yl]ethanol 3.8 g of 3-(4-bromobenzyl)-5-chloro-2-phenyl-3H-imidazole-4-carbaldehyde are dissolved in 50 ml of THF and a Grignard solution, prepared from 385 mg of magnesium turnings and 990 µl of methyl iodide in 50 ml of diethyl ether, is slowly added by syringe at RT. The mixture is stirred at RT for 3 days, then 200 ml of a 5% aqueous NaHSO$_4$ solution are added und the mixture is extracted twice using 200 ml of EA each time. The extract is dried over Na$_2$SO$_4$ and the solvent is removed in vacuo. 3.7 g of a colorless oil are obtained.

$R_f$ (DIP)=0.13 MS (DCI): 391 (M+H)$^+$.

c) 1-[3-(4-Bromobenzyl)-5-chloro-2-phenyl-3H-imidazol-4-yl]ethanone 3.7 g of 1-[3-(4-bromobenzyl)-5-chloro-2-phenyl-3H-imidazol-4-yl]ethanol is dissolved in 20 ml of acetic acid and slowly treated at 15° C. with a solution of 15.6 g of (NH$_4$)$_2$Ce(NO$_3$)$_6$ in 30 ml of water. The mixture is stirred at 10° C. for 30 minutes, then allowed to warm to RT. It is diluted with 200 ml of water and adjusted to pH=5 using NaHCO$_3$, and the product is filtered off with suction. Chromatography once each with DIP and MTB yields 2.0 g of a colorless oil.

$R_f$ (DIP)=0.42 MS (DCI): 389 (M+H)$^+$.

d) 4'-(5-Acetyl-4-chloro-2-phenylimidazol-1-ylmethyl) biphenyl-2-sulfonic Acid tert-Butylamide 21.0 g of 1-[3-(4-bromobenzyl)-5-chloro-2-phenyl-3H-imidazol-4-yl]ethanone, 2.0 g of N-tert-butyl-2-dihydroxyboran-2-ylbenzenesulfonamide, 135 mg of triphenylphosphine, 58 mg of Pd(II) acetate and 1.1 g of Na$_2$CO$_3$ are refluxed for 6 h in 50 ml of toluene and 10 ml of water. The mixture is diluted with 200 ml of EA, washed twice with 50 ml of a saturated aqueous NaHCO$_3$ solution and dried over Na$_2$SO$_4$, and the solvents are removed in vacuo. Chromatography on silica gel using DIP yields 1.4 g of a colorless oil.

MS (ES): 522 (M+H)$^+$.

e) 4'-(5-Acetyl-4-chloro-2-phenylimidazol-1-ylmethyl) biphenyl-2-sulfonamide 1.0 g of 4'-(5-acetyl-4-chloro-2-phenylimidazol-1-ylmethyl)biphenyl-2-sulfonic acid tert-butylamide and 230

μl of anisole are dissolved in 5 ml of trifluoroacetic acid and allowed to stand at RT for 24 h. The volatile constituents are then removed in vacuo and the residue is digested with 50 ml of heptane. 870 mg of an amorphous solid are obtained.

$R_f$ (MTB)=0.66 MS (ES): 466 (M+H)$^+$.

f) 4'-(5-Acetyl-4-chloro-2-phenylimidazol-1-ylmethyl)-biphenyl-2-sulfonyl-cyanamide 100 mg of 4'-(5-acetyl-4-chloro-2-phenylimidazol-1-ylmethyl)biphenyl-2-sulfonamide are reacted according to the general procedure for the preparation of sulfonylcyanamides from sulfonamides (reaction time 2 h) and 30 mg of an amorphous powder are obtained.

$R_f$ (EA/MeOH 10:1)=0.20 IR (C≡N): 2182.0 cm$^1$ MS (ES−):489 (M−H)$^-$.

EXAMPLE 30

4'-(5-Acetyl-4-methoxy-2-phenylimidazol-1-ylmethyl)biphenyl-2-sulfonylcyanamide

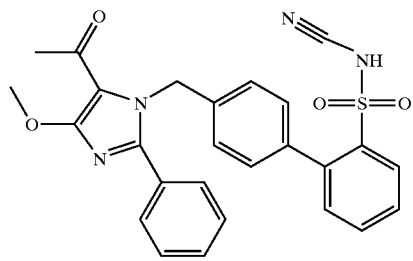

a) 4'-(5-Acetyl-4-methoxy-2-phenylimidazol-1-ylmethyl)biphenyl-2-sulfon-amide 760 mg of 4'-(5-acetyl-4-chloro-2-phenylimidazol-1-ylmethyl)biphenyl-2-sulfonamide and 650 mg of NaOH are refluxed for 22 h in 10 ml of methanol. The solvent is then removed in vacuo, the residue is taken up in 20 ml of water, and the solution is adjusted to pH=6 using a 10% aqueous HCl solution and extracted 3 times using 50 ml of EA each time. The extract is dried over Na$_2$SO$_4$ and the solvent is removed in vacuo. Chromatography on silica gel using MTB/DIP 1:1 yields 230 mg of a viscous oil.

$R_f$ (MTB/DIP 1:1)=0.31 MS (ES): 462 (M+H)$^+$.

b) 4'-(5-Acetyl-4-methoxy-2-phenylimidazol-1-ylmethyl)biphenyl-2-sulfonyl-cyanamide 210 mg of 4'-(5-acetyl-4-methoxy-2-phenylimidazol-1-ylmethyl)biphenyl-2-sulfonamide are reacted according to the general procedure for the preparation of sulfonylcyanamides from sulfonamides (reaction time 2 h) and 181 mg of an amorphous powder are obtained.

$R_f$ (EA/MeOH 10:1)=0.14 IR (C≡N): 2179.7 cm$^{-1}$ MS (ES−): 485 (M−H)$^-$.

EXAMPLE 31

4'-(2,4,5-Triphenylimidazol-1-ylmethyl)biphenyl-2-sulfonylcyanamide

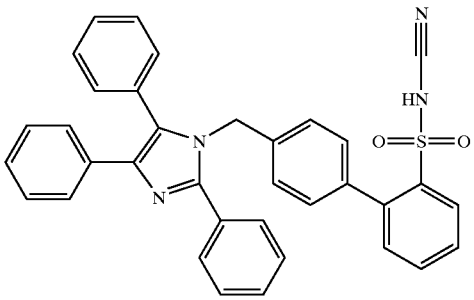

a) 4'-(2,4,5-Triphenylimidazol-1-yimethyl)biphenyl-2-sulfonic Acid Dimethylaminomethylenamide 1.5 g of 2,4,5-triphenylimidazole, 1.9 g of 4'-bromomethylbiphenyl-2-sulfonic acid dimethylaminomethylenamide (J. Med. Chem. 1995, 38, 2357) and 2.1 g of K$_2$CO$_3$ are stirred at RT for 6 days in 50 ml of DMF. The reaction mixture is poured onto 300 ml of water and extracted with 500 ml of EA. The organic phase is washed 3 times with 250 ml of a saturated aqueous NaCl solution each time and dried over Na$_2$SO$_4$, and the solvent is removed in vacuo. 2.8 g of a viscous oil are obtained.

MS (ES):597 (M+H)$^+$.

b) 4'-(2,4.5-Triphenylimidazol-1-ylmethyl)biphenyl-2-sulfonamide 1.9 g of 4'-(2,4,5-triphenylimidazol-1-ylmethyl)biphenyl-2-sulfonic acid dimethylaminomethylenamide in 20 ml of ethanol and 20 ml of a saturated aqueous HCl solution are refluxed for 3 h. The volatile constituents are removed in vacuo, the residue is stirred with 100 ml of water and the product is filtered off. 1.0 g of an amorphous powder is obtained.

$R_f$ (MTB)=0.47 MS (ES): 542 (M+H)$^+$.

c) 4'-(2,4,5-Triphenylimidazol-1-ylmethyl)biphenyl-2-sulfonylcyanamide 1.0 g of 4'-(2,4,5-triphenylimidazol-1-ylmethyl)biphenyl-2-sulfonamide are reacted according to the general procedure for the preparation of sulfonylcyanamides from sulfonamides (reaction time 2 h) and 970 mg of an amorphous powder are obtained.

$R_f$ (EA/MeOH 10:1)=0.26 IR (C≡N): 2173.5 cm$^{-1}$ MS (FAB): 567 (M+H)$^+$.

EXAMPLE 32

3'-Chloro-4'-(4-chloro-6-formyl-2-phenylimidazol-1-ylmethyl)-biphenyl-2-sulfonylcyanamide

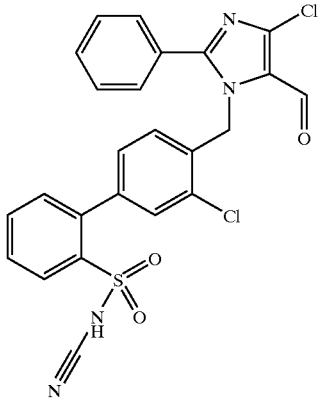

a) 4-Bromo-1-bromomethyl-2-chlorobenzene 7.1 ml of 4-bromo-2-chlorotoluene are dissolved in 20 ml of chlorobenzene and the mixture is treated in portions at 130° C. with a mixture of 9.4 g of N-bromosuccinimide and 200 mg of dibenzoyl peroxide. It is refluxed for 30 minutes, diluted with 100 ml of $CH_2Cl_2$ after cooling and washed once each with 50 ml of a saturated aqueous $Na_2SO_3$ solution and 100 ml of a saturated aqueous $NaHCO_3$ solution. The extract is dried over $Na_2SO_4$ and the solvent is removed in vacuo. 11.0 g of a pale yellow oil are obtained.

$R_f$ (EA/HEP 1:8)=0.49 MS (DCI): 283 (M+H)$^+$.

b) 3-(4-Bromo-2-chlorobenzyl)-5-chloro-2-phenyl-3H-imidazol-4-carb-aldehyde 1.5 g of 4-chloro-5-formyl-2-phenylimidazole (Chem. Pharm. Bull. 1976, 24(5), 960), 5.8 g of $K_2CO_3$ and 8.0 g of 4-bromo-1-bromomethyl-2-chloro-benzene are stirred at RT for 24 h in 50 ml of DMF. The mixture is then diluted with 250 ml of EA and washed twice with 100 ml of water each time and once with 100 ml of a saturated aqueous NaCl solution. The extract is dried over $Na_2SO_4$ and the solvents are removed in vacuo. Chromatography on silica gel using EA/HEP 1:4 yields 2.2 g of a colorless oil.

$R_f$ (EA/HEP 1:4) 0.47 MS (ES): 411 (M+H)$^+$.

c) 3'-Chloro-4'-(4-chloro-5-formyl-2-phenylimidazol-1-ylmethyl)biphenyl-2-sulfonic Acid tert-Butylamide 2.2 g of 3-(4-bromo-2-chlorobenzyl)-5-chloro-2-phenyl-3H-imidazole-4-carbaldehyd, 2.0 g of N-tert-butyl-2-dihydroxyboran-2-ylbenzenesulfonamide (J. Med. Chem. 1997, 40, 547), 140 mg of triphenylphosphine, 64 mg of Pd(II) acetate and 1.2 g of $Na_2CO_3$ are dissolved in 30 ml of toluene, 10 ml of ethanol and 10 ml of water and the solution is refluxed for 3 h. After cooling, 200 ml of a saturated aqueous $NaHCO_3$ solution are added and the mixture is extracted 3 times using 200 ml of EA each time. The extract is dried over $MgSO_4$ and the solvent is removed in vacuo. Chromatography on silica gel yields 1.5 g of a colorless foam.

$R_f$ (DIP)=0.25 MS (ES): 542 (M+H)$^+$.

d) 3'-Chloro-4'-(4-chloro-5-formyl-2-phenylimidazol-1-ylmethyl)biphenyl-2-sulfonamide 1.5 g of 3'-chloro-4'-(4-chloro-5-formyl-2-phenylimidazol-1-ylmethyl)-biphenyl-2-sulfonic acid tert-butylamide and 340 μl of anisole are dissolved in 10 ml of trifluoroacetic acid and the solution is stirred at RT for 24 h. The volatile constituents are removed in vacuo, the residue is taken up twice using 50 ml of toluene each time and the volatile constituents are again removed in vacuo. 1.5 g of a colorless foam are obtained.

$R_f$ (DIP)=0.15 MS (ES): 486 (M+H)$^+$.

e) 3'-Chloro-4'-(4-chloro-5-formyl-2-phenylimidazol-1-ylmethyl)biphenyl-2-sulfonylcyanamide 400 mg of 3'-chloro-4'-(4-chloro-5-formyl-2-phenylimidazol-1-ylmethyl)-biphenyl-2-sulfonamide are reacted according to the general procedure for the preparation of sulfonylcyanamides from sulfonamides (reaction time 2 h) and 970 mg of an amorphous powder are obtained.

$R_f$ (EA/MeOH 10:1)=0.23 IR (C≡N):2179.2 cm$^{-1}$ MS (FAB): 511 (M+H)$^+$.

1–5 is The title compound of example 33 was synthesized analogously to example 32:

EXAMPLE 33

3'-Fluoro-4'-(4-chloro-5-formyl-2-phenyl-imidazole-1-ylmethyl)-biphenyl-2-sulfonylcyanamide

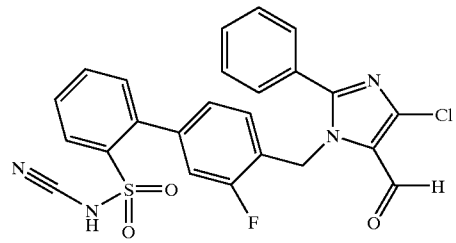

$R_f$ (EA/MeOH 10:1)=0.28 IR (C≡N):2177.7 cm$^{-1}$ MS (ES–): 493 (M–H)$^-$.

The title compound of example 34 was synthesized analogously to example 12 using 3'-chloro-4'-(4-chloro-5-formyl-2-phenyl-imidazole-1-ylmethyl)-biphenyl-2-sulfonamide (example 32 d) as the starting material:

EXAMPLE 34

3'-Chloro-4'-(4-methoxy-5-formyl-2-phenyl-imidazole-1-ylmethyl)-biphenyl-2-sulfonylcyanamide

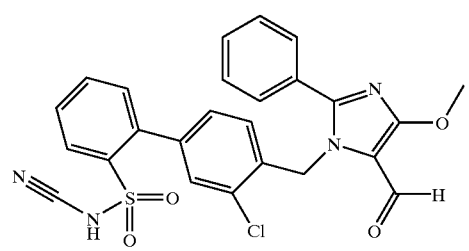

$R_f$ (EA/MeOH 10:1)=0.26 IR (C≡N): 2177.4 cm$^{-1}$ MS (ES–): 505 (M–H)$^-$.

EXAMPLE 35

3'-Chloro-4'-(4-phenoxy-5-formyl-2-phenyl-imidazole-1-ylmethyl)-biphenyl-2-sulfonylcyanamide

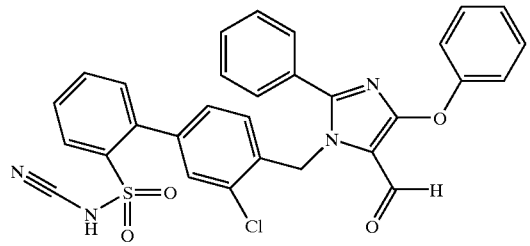

a) 3'-Chloro-4'-(4-phenoxy-5-formyl-2-phenyl-imidazole-1-ylmethyl)-biphenyl-2-sulfonamide 500 mg 3'-Chloro-4'-(4-chloro-5-formyl-2-phenyl-imidazole-1-ylmethyl)-biphenyl-2-sulfonamide (example 32 d), 116 mg phenol and 426 mg K$_2$CO$_3$ are stirred in 10 ml DMF for 8 h at 100° C. The mixture is then allowed to cool to RT, 100 ml of a saturated aqueous NaHCO$_3$ solution added and extracted 3 times with 300 ml EA each time. The organic phase is washed 3 times with 50 ml water each time, dried over Na$_2$SO$_4$ and the solvent is removed in vacuo. Chromatography on silica gel using EA/HEP 1:1 yields 150 mg of a resin-like compound.

R$_f$ (Toluol/EA 2,1)=0.39 MS (ES+): 544 (M+H)$^+$.

b) 3'-Chloro-4'-(4-phenoxy-5-formyl-2-phenyl-imidazole-1-ylmethyl)-biphenyl-2-sulfonylcyanamide 145 mg 3'-Chloro-4'-(4-phenoxy-5-formyl-2-phenyl-imidazole-1-ylmethyl)-biphenyl-2-sulfonamide are reacted according to the general procedure for the preparation of sulfonylcyanamides using sulfonamides (reaction time 2 h), and 99 mg of a foam are obtained.

R$_f$ (EA/MeOH 10:1)=0.35 IR (C≡N): 2180.4 cm$^{-1}$ MS (ES−): 567 (M−H)$^-$.

The title compounds of examples 36–38 are synthesized analogously to example 11:

EXAMPLE 36

4'-[4-Chloro-5-formyl-2-(4-chlorphenyl)-imidazole-1-ylmethyl]-biphenyl-2-sulfonylcyanamide

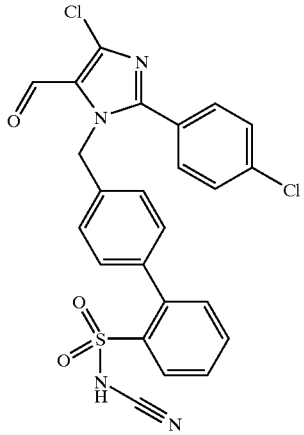

R$_f$(EA/MeOH 10:1)=0.28 mp 160–187° C. MS (ES)=511 (M+1)$^+$.

EXAMPLE 37

4'-[4-Chloro-5-formyl-2-(4-methoxyphenyl)-imidazole-1-ylmethyl]-biphenyl-2-sulfonylcyanamide

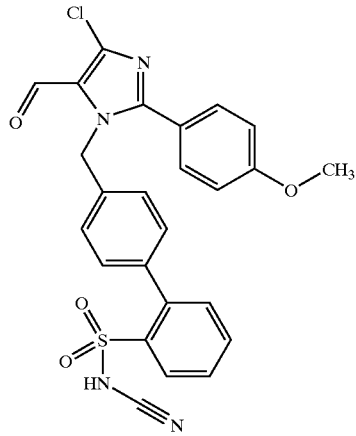

R$_f$(EA/MeOH 10:1)=0.31 mp 110–126° C. MS (ES)=507 (M+1)$^+$.

EXAMPLE 38

4'-[4-Chloro-5-formyl-2-(2,6-difluorphenyl)-imidazole-1-ylmethyl]-biphenyl-2-sulfonylcyanamide

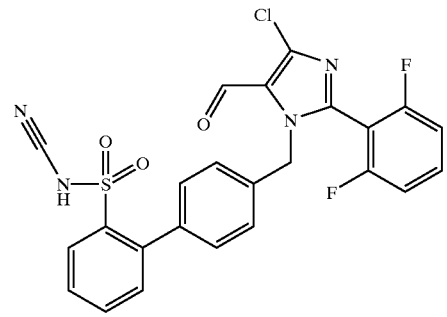

R$_f$(EA/MeOH 10:1)=0.25 mp 164–178° C. MS (ES)=513 (M+1)$^+$.

Pharmacological Data

Inhibition of the Na$^+$-dependent Cl$^-$/HCO$_3^-$ Exchanger (NCBE) in Human Endothelial Cells Human endothelial cells (ECV-304) were detached from culture bottles with the aid of trypsin/EDTA buffer (0.05/0.02% in phosphate buffer) and, after centrifugation (100 g, 5 min), taken up in a buffered salt solution (mmol/l: 115 NaCl, NH$_4$Cl, 5 KCl, 1 CaCl$_2$, 1 MgSO$_4$, 20 N-(2-hydroxyethyl)piperazine-N'-2-ethanesulfonic acid (HEPES), 5 glucose and 1 μ/l of bovine serum albumin; pH 7.4). This cell suspension was incubated at 37° C. for 20 min with 5 μM BCECF-acetoxymethyl ester. The cells were then washed and resuspended in a sodium- and bicarbonate-free buffer solution (mmol/l: 5 HEPES, 133.8 choline chloride, 4.7 KCl, 1.25 MgCl$_2$, 0.97 K$_2$HPO$_4$, 0.23 KH$_2$PO$_4$, 5 glucose; pH 7.4).

For subsequent fluorescence measurement in an FLIPR (Fluorescent Imaging Plate Reader) 100 μl of this cell suspension having 20,000 cells in each case were pipetted per well into a 96-well microtiter plate and this microtiter plate was centrifuged (100 g, 5 min).

In the FLIPR, 100 µl of buffer solution in each case were then removed from a further pretreated microtiter plate and pipetted into each of the 96 wells of the measurement plate. A bicarbonate- and sodium-containing buffer solution (mmol/l: 5 HEPES, 93.8 NaCl, 40 NaHCO$_3$, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) which contained 50 µM HOE 642 was used for a 100% control, i.e. a recovery of the intracellular pH (pH$_i$) via the NCBE. For a 0% control, i.e. no pH$_i$ recovery at all, the bicarbonate-free, sodium-containing buffer solution (mmol/l: 5 HEPES, 133.8 NaCl, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) was employed, to which 50 µM HOE 642 were likewise added. The compounds according to the invention were added to the sodium- and bicarbonate-containing solution in various concentrations.

After addition of the buffer solutions to the dye-loaded, acidified cells in the measurement plate, the rise in the fluorescence intensity which corresponded to a rise in the pH, in each well of the microtiter plate was determined. The kinetics were in this case recorded at 35° C. for a period of 2 minutes.

The increase in the fluorescence intensities for different concentrations of the compounds according to the invention was related to the two controls and from this the inhibitory action of the substances was determined.

Results
Residual Activity of the NCBE at an Inhibitor Concentration of 10 µM

| Example | Residual activity in % |
|---|---|
| 1 | 17.7 |
| 2 | 39.6 |
| 3 | 74.1 |
| 4 | 39.7 |
| 5 | 43.2 |
| 6 | 58.6 |
| 7 | 72.1 |
| 8 | 60.8 |
| 9 | 31.6 |
| 10 | 21.6 |
| 11 | 15.0 |
| 12 | 20.8 |
| 13 | 89.5 |
| 14 | 47.3 |
| 15 | 55.7 |
| 16 | 11.5 |
| 17 | 39.1 |
| 18 | 45.8 |
| 19 | 21.5 |
| 20 | 19.5 |
| 21 | 42.6 |
| 22 | 34.2 |
| 23 | 31.6 |
| 24 | 29.2 |
| 25 | 70.8 |
| 26 | 65.3 |
| 27 | 50.0 |
| 28 | 30.5 |
| 29 | 39.6 |
| 30 | 48.8 |
| 31 | 36.5 |
| 32 | 7.8 |
| 33 | 7.6 |
| 34 | 5.5 |

-continued

| Example | Residual activity in % |
|---|---|
| 35 | 3.2 |
| 36 | 7.8 |
| 37 | 16.8 |
| 38 | 8.6 |

What is claimed is:
1. A method for the treatment of an illness in which cell proliferation is a primary or secondary cause, which comprises administering to a host in need of such treatment an effective amount of at least one compound of the formula I:

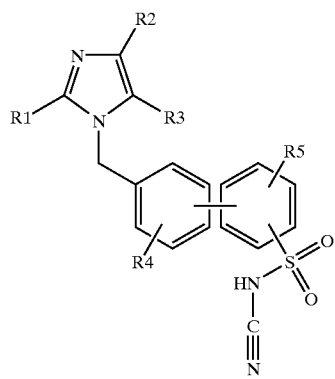

or a physiologically tolerable salt thereof,
in which the symbols have the following meaning:
R1 is hydrogen, alkyl having 1, 2, 3, 4, 5, 6, 7 or 8 carbon atoms or —C$_a$H$_{2a}$-phenyl,
said —C$_a$H$_{2a}$-phenyl being unsubstituted or substituted by 1–3 substituents selected from the group consisting of F, Cl, Br, I, CF$_3$, methyl, methoxy, hydroxyl and NR(8)R(9);
R(8) and R(9) independently of one another are H or (C$_1$–C$_4$)alkyl;
a is zero, 1 or 2;
or
R1 is —C$_b$H$_{2b}$-(C$_1$–C$_9$)heteroaryl,
which is unsubstituted or substituted by 1–3 substituents selected from the group consisting of F, Cl, Br, I, CF$_3$, CH$_3$, methoxy, hydroxyl and NR(10)R(11);
R(10) and R(1) independently of one another are H or (C$_1$–C$_4$)alkyl;
b is zero, 1 or 2;
or
R1 is —C$_d$H$_{2d}$-(C$_3$–C$_7$)cycloalkyl;
d is zero, 1 or 2;
R2 and R3 independently of one another are hydrogen, F, Cl, Br, I, CF$_3$, —C≡N, —NO$_2$, CH$_2$OR17, CO-R6 or O-R7;
R17 is hydrogen or alkyl having 1, 2, 3, 4, 5, 6, 7 or 8 carbon atoms;
R6 is hydrogen, alkyl having 1, 2, 3, 4, 5, 6, 7 or 8 carbon atoms, OR30 or phenyl,
said phenyl being unsubstituted or substituted by 1–3 substituents selected from the group consisting of F, Cl, Br, I, CF$_3$, methyl, methoxy, hydroxyl and NR(31)R(32);
R(31) and R(32) independently of one another are H or (C$_1$–C$_4$)-alkyl;

R30 is hydrogen or alkyl having 1, 2, 3, 4, 5, 6, 7 or 8 carbon atoms;

R7 is hydrogen, alkyl having 1, 2, 3, 4, 5, 6, 7 or 8 carbon atoms, phenyl,
said phenyl being unsubstituted or substituted by 1–3 substituents selected from the group consisting of F, Cl, Br, I, $CF_3$, methyl, methoxy, hydroxyl and NR(12)R(13);
R(12) and R(13)
independently of one another are H or $(C_1-C_4)$-alkyl;

or

R7 is $(C_1-C_9)$heteroaryl,
which is unsubstituted or substituted by 1–3 substituents selected from the group consisting of F, Cl, Br, I, $CF_3$, $CH_3$, methoxy, hydroxyl and NR(14)R(15);
R(14) and R(15)
independently of one another are H or $(C_1-C_4)$-alkyl;

or

R2 and R3
independently of one another are alkyl having 1, 2, 3, 4, 5, 6, 7 or 8 carbon atoms, cycloalkyl having 3, 4, 5, 6 or 7 carbon atoms or —$C_gH_{2g}$-phenyl,
said —$C_gH_{2g}$-phenyl being unsubstituted or substituted by 1–3 substituents selected from the group consisting of F, Cl, Br, I, $CF_3$, methyl, methoxy, hydroxyl and NR(18)R(19);
R(18) and R(19)
independently of one another are H or $(C_1-C_4)$alkyl;
g is zero, 1 or 2;

or

R2 and R3
independently of one another are —$C_lH_{2l}$-$(C_1-C_9)$ heteroaryl,
which is unsubstituted or substituted by 1–3 substituents selected from the group consisting of F, Cl, Br, I, $CF_3$, $CH_3$, methoxy, hydroxyl and NR(20)R(21);
R(20) and R(21)
independently of one another are H or $(C_1-C_4)$-alkyl;
l is zero, 1 or 2;

or

R2 and R3
independently of one another are $SO_n$-R22;
n is zero, 1 or 2;
R22 is alkyl having 1, 2, 3, 4, 5, 6, 7 or 8 carbon atoms, cycloalkyl having 3, 4, 5, 6 or 7 carbon atoms or —$C_sH_{2s}$-phenyl,
said –$C_sH_{2s}$-phenyl being unsubstituted or substituted by 1–3 substituents selected from the group consisting of F, Cl, Br, I, $CF_3$, methyl, methoxy, hydroxyl and NR(34)R(35);
R(34) and R(35)
independently of one another are H or $(C_1-C_4)$-alkyl;
s is zero, 1 or 2;

R4 and R5
independently of one another are hydrogen, alkyl having 1, 2, 3, 4, 5, 6, 7 or 8 carbon atoms, F, Cl, Br, I, $CF_3$, —C≡N, —$NO_2$, $SO_p$-R16, CO-R23 or O-R24;
p is zero, 1 or 2;
R16 is alkyl having 1, 2, 3, 4, 5, 6, 7 or 8 carbon atoms or phenyl,
said phenyl being unsubstituted or substituted by 1–3 substituents selected from the group consisting of F, Cl, Br, I, $CF_3$, methyl, methoxy, hydroxyl and NR(26)R(27);
R(26) and R(27)
independently of one another are H or $(C_1-C_4)$-alkyl;
R23 is hydrogen, alkyl having 1, 2, 3, 4, 5, 6, 7 or 8 carbon atoms or OR25;
R25 is hydrogen, alkyl having 1, 2, 3, 4, 5, 6, 7 or 8 carbon atoms;
R24 is hydrogen, alkyl having 1, 2, 3, 4, 5, 6, 7 or 8 carbon atoms or phenyl,
said phenyl being unsubstituted or substituted by 1–3 substituents selected from the group consisting of F, Cl, Br, I, $CF_3$, methyl, methoxy, hydroxyl and NR(28)R(29);
R(28) and R(29)
independently of one another are H or $(C_1-C_4)$-alkyl.

2. A method as claimed in claim 1, which comprises treating atherosclerosis.

3. A method as claimed in claim 1, which comprises treating a late diabetic complication.

4. A method as claimed in claim 1, which comprises treating a carcinomatous disorder.

5. A method as claimed in claim 1, which comprises treating a fibrotic disorder.

6. A method as claimed in claim 5, wherein the fibrotic disorder is pulmonary fibrosis.

7. A method as claimed in claim 5, wherein the fibrotic disorder is hepatic fibrosis.

8. A method as claimed in claim 5, wherein the fibrotic disorder is renal fibrosis.

9. A method as claimed in claim 1, which comprises treating organ hypertrophy.

10. A method as claimed in claim 9, which comprises treating prostate hypertrophy.

11. A method as claimed in claim 1, which comprises treating organ hyperplasia.

12. A method as claimed in claim 11, which comprises treating prostate hyperplasia.

* * * * *

UNITED STATES PATENT AND TRADEMARK OFFICE
CERTIFICATE OF CORRECTION

PATENT NO.    : 6,486,189 B2  
DATED         : November 26, 2002  
INVENTOR(S)   : Heinz-Werner Kleemann et al.

It is certified that error appears in the above-identified patent and that said Letters Patent is hereby corrected as shown below:

Column 48,  
Line 48, "R(10) and R(1)" should read -- R(10) and R(11) --.

Column 49,  
Line 34, "-C$_1$H$_{21}$-(C$_1$-C$_9$)" should read -- C$_l$H$_{2l}$-(C$_1$-C$_9$) --.  
Line 41, "I is zero" should read -- l is zero --.

Signed and Sealed this

Fifteenth Day of April, 2003

JAMES E. ROGAN  
*Director of the United States Patent and Trademark Office*